(12) United States Patent
Bynum et al.

(10) Patent No.: US 6,841,792 B2
(45) Date of Patent: Jan. 11, 2005

(54) ATR CRYSTAL DEVICE

(75) Inventors: Kevin C. Bynum, Yonkers, NY (US); Abe S. Kassis, Yonkers, NY (US)

(73) Assignee: Euro-Celtique, S.A. (LU)

( * ) Notice: Subject to any disclaimer, the term of this patent is extended or adjusted under 35 U.S.C. 154(b) by 0 days.

(21) Appl. No.: 10/108,188

(22) Filed: Mar. 27, 2002

(65) Prior Publication Data

US 2002/0190213 A1 Dec. 19, 2002

Related U.S. Application Data

(60) Provisional application No. 60/279,187, filed on Mar. 27, 2001.

(51) Int. Cl.$^7$ .......................... G06K 11/00; G06K 5/00
(52) U.S. Cl. ........................ 250/556; 356/436; 356/244
(58) Field of Search ........................ 250/341.8, 339.11, 250/216, 573, 576, 226, 228, 227.25, 339.07, 343, 373; 356/244, 246, 300, 432, 436, 445, 450–451; 128/665

(56) References Cited

U.S. PATENT DOCUMENTS

| | | | | | |
|---|---|---|---|---|---|
| 3,902,807 | A | * | 9/1975 | Fleming et al. | ............. 356/300 |
| 4,835,389 | A | * | 5/1989 | Doyle | ........................ 250/343 |
| 5,051,551 | A | * | 9/1991 | Doyle | ...................... 250/341.2 |
| 5,170,056 | A | | 12/1992 | Berard et al. | ................ 250/341 |
| 5,172,182 | A | * | 12/1992 | Sting et al. | .................. 356/244 |
| 5,436,454 | A | * | 7/1995 | Bornstein et al. | ...... 250/339.12 |
| 5,754,722 | A | * | 5/1998 | Melling | ....................... 385/115 |
| 6,128,091 | A | * | 10/2000 | Uchida et al. | .............. 356/432 |
| 6,174,497 | B1 | | 1/2001 | Roinestad et al. | ....... 422/82.05 |
| 6,444,982 | B1 | | 9/2002 | Mitchell et al. | ............. 250/311 |
| 6,558,957 | B1 | | 5/2003 | Roinestad et al. | .......... 436/164 |

FOREIGN PATENT DOCUMENTS

| | | |
|---|---|---|
| JP | 07294421 | 11/1995 |
| WO | 0116582 | 3/2001 |

* cited by examiner

*Primary Examiner*—Stephone B. Allen
*Assistant Examiner*—Patrick J. Lee
(74) *Attorney, Agent, or Firm*—Davidson, Davidson & Kappel, LLC

(57) ABSTRACT

The present invention includes an ATR crystal system comprising: an ATR crystal, one face of the ATR crystal forming a portion of an interior surface of a containment vessel, a radiation source for creating a beam or radiation, the radiation sources optically connected to an input area of the ATR crystal; and a detector for recording the beam of radiation, the detector optically connected to an output area of the ATR crystal. The present invention also includes a method of sample analysis utilizing an ATR crystal embedded in a containment vessel comprising the steps of: providing a containment vessel having an ATR crystal embedded therein; generating a monochromatic beam of light; transmitting the beam to an input of the ATR crystal; transmitting the beam from an output of the ATR crystal to a detector; and recording a signal from the detector.

108 Claims, 14 Drawing Sheets

ATR CRYSTAL DEVICE

This application claims the benefit under 35 U.S.C. §119(e) of prior-filed, copending U.S. Provisional Patent Application No. 60/279,187, filed on Mar. 27, 2001, the entire disclosure of which is hereby incorporated by reference.

FIELD OF THE INVENTION

The present invention relates to the field of spectroscopic detectors.

BACKGROUND OF THE INVENTION

ATR (Attenuated Total Reflectance) spectroscopy is a technique that is based on molecular vibration and the curvature of light beams when passing through different mediums. An ATR spectrum is generated by transmitting radiation, which can be IR (from about 0.1 cm to about $7.5 \times 10^{-5}$ cm), VIS (from about $7.0 \times 10^{-5}$ to about $4.0 \times 10^{-5}$ cm), or UV (from about $4.0 \times 10^{-5}$ cm to about $2.2 \times 10^{-5}$ cm), through an optical crystal in contact with a sample and then determining what portion of the incident radiation is attenuated by the sample at a particular wavelength. ATR spectrometry is used extensively in clinical assays, medical diagnostics, and laboratory testing. Since the depth of penetration for the evanescent wave in ATR spectrometry is shallow, there is a low incidence of Fresnel Reflection. Thus, reliable spectral analysis of murky, semisolid, turbid, and optically dense solutions is possible with ATR spectrometry.

When light travels from one medium to another, a speed change results that causes the light to bend. The amount that a beam of light bends on passing from a first medium to a second medium can be determined by calculating the refractive index of both mediums, defined as the ratio of the speed of light in a vacuum to the speed of light in a medium ($n=c/v$), and applying Snell's Law. Snell's Law: $n_1 \sin \theta_1 = n_2 \sin \theta_2$ (where $n_1$ is the refractive index of the first medium, $n_2$ is the refractive index of the second medium, $\sin \theta_1$ is the angle of light to the normal in the first medium, and $\sin \theta_2$ is the refracted angle of the light to the normal in the second medium), calculates the amount of curvature of the beam of light on moving from the first medium to the second medium. Pursuant to Snell's Law, when the beam of light impinges an interface between the first and second medium at or above a critical angle, defined as $\sin_{crit}$ (or $\theta_{crit}) = \sin^{-1} n_2/n_1$ there is no refracted ray, i.e., the incident light is totally internally reflected, and an evanescent wave is generated.

In ATR spectrometry, a sample is measured by passing a beam of light through an optical crystal, which can be mounted on a probe. The beam, which, for example, can be UV, IR, or VIS, is directed onto the optical crystal at an angle of incidence such that all incident light undergoes total internal reflection. When the beam undergoes total internal reflection, an electro-magnetic radiation field, described by N. J. Harrick (1965) as an evanescent wave, extends beyond the surface of the crystal into the sample next to the crystal. The depth of penetration of the evanescent wave, which is generally quite shallow, is a function of the refractive index of the crystal material, refractive index of the sample material, angle of incidence of the beam, and wavelength of the light. In regions of the spectrum where the sample absorbs energy, the evanescent wave is attenuated and the attenuated energy is passed back to the beam of light. The beam of light then exits the optical crystal and impinges a detector. The detector records the attenuated beam, which can then be transformed to generate a spectrum, e.g., an absorption spectra.

Detectors used in spectroscopy generally fall into two classes, photographic detectors, in which radiation impinges upon an unexposed photographic film, and electronic detectors, in which the radiation impinges upon a detector and is converted into an electrical signal. Electronic detectors provide the advantage of increased speed and accuracy, as well as the ability to convert the spectral data into an electronic format, which can be displayed, processed, and/or stored. Examples of electronic detectors include photomultiplier tubes and photodetectors. Photomultiplier tubes are quite sensitive, but are relatively large and expensive. Photodetectors provide the advantage of reduced size and cost. Some examples of photodetectors are pin diode detectors, charge coupled device detectors, and charge injection device detectors.

According to the Beer-Lambert Law, a linear relationship exists between the spectrum and the concentration of a sample. In mathematical terms: $A = \epsilon bc$, where A is the absorbance value of a sample at a specific wavelength, b is the pathlength through the sample, c is the concentration, and $\epsilon$ is the absorbency coefficient of the material at the specific wavelength. In order to determine the relationship between the spectrum and the concentration, an instrument measures a set of standard samples, which reflect the compositions of unknown samples as closely as possible and span the expected range of concentrations and compositions of the unknowns. The measurements of the standard samples along with measured data from a training set are then used to create a set of calibration equations. However, in order to apply the equations to a set of unknown samples, finding the constant for the absorptivity coefficient is necessary. As the absorptivity coefficient for a given compound at a selected wavelength is constant, a least squares regression method, classical least squares regression method, or inverse least squares regression method can be used to solve the equation. Once the calibration equations have been solved, calculation of quantities or properties of unknown samples is possible. However, in order for the quantities and properties to be predicted accurately, the unknown samples should be measured under the same conditions. Spectrometers are ideal measurement devices because unlike other methods, which give single point measurements for each calibration and unknown sample, the spectrum of a sample contains many data points. Furthermore, every response value in a spectrum has some relation to the properties or constituents that make up the sample.

Dissolution testing is required for all solid oral pharmaceutical dosage forms in which absorption of the drug is necessary for the product to exert the desired therapeutic effect. One way to calculate the amount of dissolution of a substance in a medium is by creating and solving a calibration equation that accurately predicts the quantity of the constituents of interest.

The U.S. Pharmacopoeia (USP) is one well-known standard source of information that provides for dissolution and drug release testing in the majority of monographs for such dosage forms. Exceptions are for tablets meeting a requirement for completeness of solution or for rapid (10 to 15 minutes) disintegration of soluble or radiolabled drugs. The apparatus and procedure conform to the requirements and specifications given, e.g., USP 23rd edition Chapter 711 (Dissolution) pages 1791–1793. Dissolution testing serves as a measure of quality control, stability and uniformity as well as a means by which to correlate in-vitro with in-vivo drug release characteristics. Current USP dissolution methods most commonly employ a temperature programmable water bath, maintained at about 37° C., in which sample vessels are submerged. These vessels contain a predetermined volume of a dissolution media and a mechanism to agitate the contents of the vessel. This may be accomplished with a rotating basket attached to a shaft or with a paddle that is also attached to a shaft, both of which are generally described in USP 23rd edition Chapter 711 (Dissolution) pages 1791–1793. The solid dosage form is placed into the media-filled vessel at time zero, and specific vessel temperature and mixing speeds are maintained as dissolution of the dosage form in the medium is monitored over time.

A number of systems are currently used to perform dissolution testing of dosage forms. For example, it is known to use a pumping system which removes dissolution media from the vessel and then provides it to a spectrometer for analysis. However, this system has the disadvantage of removing the dissolution media from the vessel during dissolution, thereby, changing the dissolution conditions. It is also known to use fiber optic flow cell probes disposed within the dissolution media to monitor dissolution. However, such probes have apertures which may become clogged, thus, affecting the dissolution measurements.

SUMMARY OF THE INVENTION

In accordance with a first embodiment of the present invention, an ATR crystal system is provided which includes an ATR crystal, a containment vessel, a radiation source, and a detector. One face of the ATR crystal forms a portion of an interior surface of the containment vessel. The radiation source generates a beam of radiation, and is optically connected to an input of the ATR crystal. The detector optically connected to an output of the ATR crystal, and records the beam of radiation.

In accordance with a second embodiment of the present invention, the ATR crystal system is incorporated into an apparatus and method for determining a dissolution profile of a pharmaceutical dosage form containing a releasable quantity of a therapeutically active agent. In accordance with this embodiment, the vessel includes a dosage form immersed in a dissolution media, and processor is coupled to the detector. The processor receives information from the ATR crystal as the dissolution of the dosage form in the dissolution medium proceeds, analyzes the information, and generates a dissolution profile of the dosage form.

In accordance with a third embodiment of the present invention, a method of sample analysis utilizing an ATR crystal in a containment vessel is provided which comprises the steps of providing a containment vessel having an ATR crystal, the ATR crystal forming a portion of an interior surface of the vessel; generating a monochromatic beam of light; transmitting the beam to an input of the ATR crystal; transmitting the beam from an output of the ATR crystal to a detector; and recording a signal from the detector.

In accordance with a fourth embodiment of the present invention, an apparatus and method for determining a dissolution profile of a pharmaceutical dosage form containing a releasable quantity of a therapeutically active agent is provided. A vessel for immersing a pharmaceutical dosage form in a dissolution medium is provided along with an elongated probe which includes an ATR crystal. The elongated probe is disposed in the vessel such that the ATR crystal immersed in the dissolution medium. A radiation source for creating a beam of radiation is optically connected to an input of the ATR crystal, and a detector is optically connected to an output of the ATR crystal to record the beam of radiation. A processor is coupled to the detector, and receives information from the detector as the dissolution of the dosage form in the dissolution medium proceeds, analyzes the information, and generates a dissolution profile of the dosage form.

In accordance with a fifth embodiment of the present invention, an apparatus is provided which includes a dissolution vessel and an ATR crystal, wherein one face of the ATR crystal forms a portion of an interior surface of the dissolution vessel.

DETAILED DESCRIPTION OF THE PREFERRED EMBODIMENTS

Figure 1A:
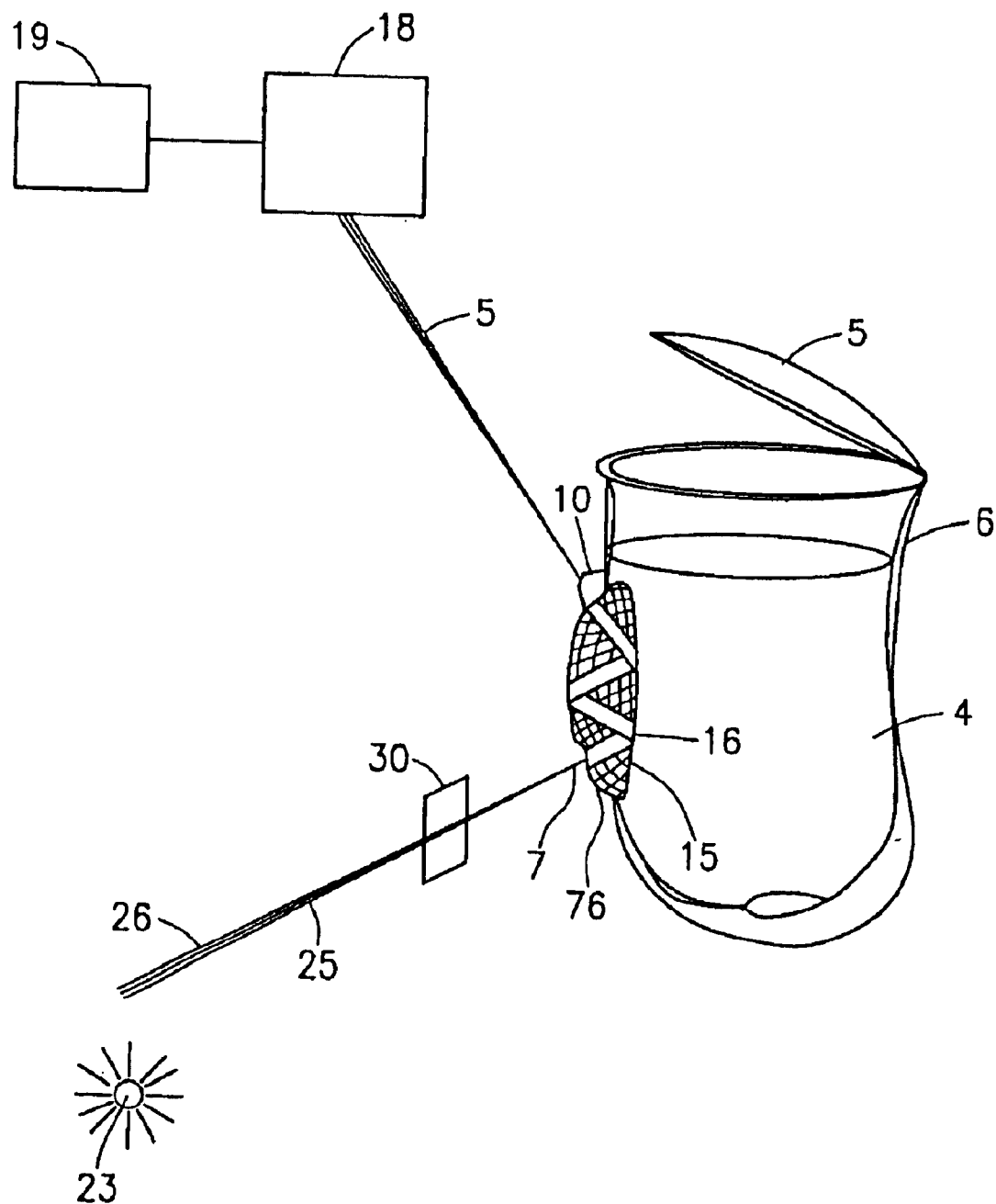
FIGS. 1(a,b) illustrates alternative embodiments of the present invention in which an ATR crystal is embedded in a vessel, and is coupled between a radiation source and a detector via a first connecting device, and a second connecting device, respectively.

Current ATR devices can detect spectral data from samples with a high incidence of Fresnel Reflection. However, the results are often inaccurate due to the general hydrodynamic disruption that occurs when a probe is placed within a sample medium (especially if the sample is aqueous).

In accordance with a first embodiment of the present invention, an embedded ATR crystal system is provided. The system includes an ATR crystal. One face of the ATR crystal forms a portion of the interior surface of a containment vessel and is shaped to fit in an aperture of the containment vessel. A radiation source is optically connected to an input of the ATR crystal and a detector is optically connected to an output of the ATR crystal. The containment vessel also includes a second aperture for receiving a sample and dissolution media. In use a sample is placed in the containment vessel, which includes dissolution media. The radiation source then generates a beam of light, which enters the crystal. The beam of light is redirected in the crystal so that the light impinges the interface, located between the crystal and the dissolution media in the containment vessel, at least once before exiting the crystal. So long as the beam impinges the interface between the crystal and the composition at an angle of incidence at or above a critical angle, an evanescent wave is generated. The composition attenuates the evanescent wave, and the attenuated energy from the wave passes back to the beam. On exiting the crystal, the beam intersects a detector, which records the beam and this detected beam is then converted into an absorbance spectra.

In accordance with a second embodiment of the present invention, an apparatus for determining a dissolution profile of a pharmaceutical dosage form containing a releasable quantity of a therapeutically active agent is provided, wherein the dosage form is immersed in a dissolution medium contained in a vessel. The apparatus includes a vessel for immersing a pharmaceutical dosage form in a dissolution medium. The vessel has an ATR crystal, and one face of the ATR crystal forms a portion of an interior surface of the vessel and is shaped to fit in an aperture in a side of the containment vessel. A radiation source, which creates a beam of radiation, is optically connected to an input of the ATR crystal. A detector for recording the beam of radiation is optically connected to an output of the ATR crystal. A processor is coupled to the detector, and the processor receives information from the ATR crystal as the dissolution of the dosage form in the dissolution medium proceeds, analyzes the information, and generates a dissolution profile of the dosage form. Most preferably, the processor receives, analyzes, and displays the dissolution profile as dissolution in the dissolution medium proceeds. Software for providing such functionality is described, for example, in PCT US00/23800, entitled "In Situ Methods for Measuring the Release of a Substance from a Dosage Form," the entire disclosure of which is hereby incorporated by reference.

In using this apparatus, an operator preferably performs a baseline correction by taking measurements without a sample present in the vessel to obtain a baseline spectra. Thereafter, the operator places a dissolution medium and a sample material in the containment vessel. The apparatus is then used to generate spectral data from the dissolution media. The baseline spectra is then subtracted from the spectral data to provide the spectra of the dissolution medium.

In the first and second embodiments described above, by placing the crystal in the wall of the containment vessel, hydrodynamic disruption is reduced, resulting in more accurate measurements of spectral data. Additionally, multiple measurements can be taken without having to readjust the ATR crystal. Moreover, since the location of the ATR crystal is fixed, similar conditions for measuring standard and unknown samples are facilitated. Preferably, the ATR crystal is secured to the wall of the containment vessel.

In accordance with a third embodiment of the present invention, an ATR crystal is provided in an elongated probe. The elongated probe is configured to direct a beam of radiation to the ATR crystal and is disposed within a dissolution vessel. Radiation is optically connected to an input of the ATR crystal; and a detector is optically connected to an output of the ATR crystal. In use, the dissolution vessel includes dissolution media and a dosage form is submerged in the dissolution media. The radiation source generates a beam of light, which is directed to the ATR crystal through the probe. The probe may be constructed of chalcogenide fiber or Fused Silica Fiber. Preferably, embedded in the probe are two internal connection devices that are attached to a first and second connecting devices, which, in turn, are coupled to the radiation source and detector, respectively. A glass with a refractive index lower than the probe may coat the outer surface of the probe. Thus, the probe directs the light to and from the crystal with minimal interference. On entering the crystal, the beam of light is redirected so that the light impinges the interface between the crystal and the composition in the containment vessel at least once before exiting the crystal. So long as the beam impinges the interface between the crystal and the composition at an angle of incidence at or above a critical angle, an evanescent wave is generated. The composition attenuates the evanescent wave, and the attenuated energy from the wave passes back to the beam. On exiting the crystal, the beam intersects a detector, which records the beam. The detected beam can then be used to generate a spectrum, which, in turn, is processed to provide a dissolution profile of the dosage form in the dissolution medium.

Preferably, the probe is constructed of chalcogenide fiber, e.g., from glass composed of arsenic, selenium, and tellurium (AsSeTe glass). Chalcogenide fiber performs well in the mid-IR range, transmitting across a substantial part of the mid-IR region, namely 900–5000 nm. The probe can also be clad with a glass of lower refractive index to prevent escape or "leakage" of radiation from the fiber, which results in more precise spectral readings. In the UV/Vis range, Fused Silica Fiber may be used as the ATR crystal.

The probe can be configured to form a seal between the outer surface of the probe and an opening of the containment vessel (or an opening in a containment vessel cover), thus, minimizing loss of the material in the containment vessel due to spillage or evaporation. A securing device, e.g., a screw, can be used to fix the location of the probe with respect to the containment vessel.

Due to the low incidence of Fresnel Reflection associated with ATR crystals, analysis of murky, turbid, and semisolid substances are possible. Moreover, spectra can be obtained from liquid samples having a high molar extinction coefficient, such as pastes and other viscous mixtures.

The radiation source can be, but is not limited to, a QTH lamp, a deuterium lamp, a light emitting diode, or a laser. The radiation source can also be a Xenon Lamp, a Mercury Xenon Lamp, a Xenon Flash Lamp, a Metal Halide Lamp, a GaAs Infrared LED, a GaAlA Infrared LED, GaAlA Infrared LED, or a GaAAs Infrared LED (produced by Hamamatsu Corporation). The differing sources allow spectroscopic analysis in the ultraviolet and visible regions as well as the infrared regions, thus, facilitating the analysis of dyes and other strongly absorbing water soluble substances.

In embodiments where the light source is not a monochromatic-light source, a filter, for example, a monochromator, a spectrograph, a linear variable filter, a bandpass filter, or an interference filter is provided either between the radiation source and the ATR crystal, or between the ATR crystal and detector. The filter can also be a monochromator-filter type device, rotating tilting filter wheels, spinning filter wheel, AOTF(Acousto Optic Tunable Filter), pre-dispersive grating monochromator, or post-dispersive grating monochromator. The filter acts to separate a monochromatic beam of light from a polychromatic beam of light, thus, allowing spectral analysis.

One or more connecting devices can transfer the beam of light from a radiation source to the ATR crystal or probe, and from the ATR crystal or probe to the detector. One or more mirrors can also transfer the beam of light from the radiation source to the ATR crystal or probe, and from the ATR crystal or probe to the detector. The first and second connecting devices can be rigid wave tubes or fiber optic cables. Both the rigid wave tubes and fiber optic cables guide the beam of light from a source to a destination, however, the fiber optic cables have greater flexibility and are less prone to damage. Also, fiber optic cables can be embedded in the interior of the probe. Mirrors are generally less expensive than wave tubes or fiber optic guides and can be used in environments not conducive to wave tubes or fiber optic guides. A UV spot light source produced by Hamamatsu Corporation can also be used as the radiation source and connected to the crystal.

The probe can be constructed of or coated in an inert material, e.g., TEFLON (polytetrafluorethylene ("PTFE")), fluoroplastic, NALGENE, or TEFLON fluoropolymer resin, and contain one or more internal connecting devices, which are connected to the first and second connecting devices and the ATR crystal. In order to analyze radioactive or highly corrosive substances, the probe may also be constructed and/or coated with lead or steel. Instead of using internal connecting devices, the first and second connecting devices can be embedded in the probe. Thus, the exterior surface of the probe protects the connecting devices from a corrosive composition.

The containment vessel preferably can be constructed of or coated in an inert material, e.g., TEFLON (polytetrafluorethylene ("PTFE")), fluoroplastic, NALGENE, or TEFLON fluoropolymer resin, thus, allowing analysis of corrosive materials. Preferably, in order to prevent loss of the composition, a cover covers and forms a seal with the opening in the vessel. In order to analyze radioactive or highly corrosive substances, the containment vessel may also be constructed and/or coated with lead or steel. The containment vessel can also be constructed of glass, PYREX, plastic or other materials typically used to hold non-corrosive substances.

The embedded ATR may be composed of ZnSe, Ge, SeAs, Cds, CdTe, CsI, C, InSb, Si, Sapphire ($Al_2O_3$), Anneled Glass, borosilicate crown glass, BK7 Anneled Glass, UBK7 Annealed Glass, LaSF N9 Anneled Glass, BaK1 Annealed Glass, SF11 Annealed Glass, SK11 Annealed Glass, SF5 Annealed Glass, Flint Glass, F2 Glass, Optical Crown Glass, Low-Expansion Borosilicate Glass(LEBG), Pyrex, Synthetic Fused Silica (amorphous silicon dioxide), Optical Quality Synthetic Fused Silica, UV Grade Synthetic Fused Silica, ZERODUR, AgBr, AgCl, KRS-5 (a TlBr and TlCl compound), KRS-6 (a TlBr and TlCl compound), ZnS, $ZrO_2$, AMTIR, or diamond.

The entire ATR crystal or a portion thereof can be coated with a metallic coating, dielectric coating, bare aluminum, protected aluminum, enhanced aluminum, UV-enhanced aluminum, internal silver, protected silver, bare gold, protected gold, MAXBRIte, Extended MAXBRIte, Diode Laser MAXBRIte, UV MAXBRIte, or Laser Line MAX-R. The coating increases the amount of light reflected, thus, improving the accuracy of the data. Furthermore, the coating can be a material that only reflects a specific wavelength of light.

The ATR crystal can have a variety of shapes including, but not limited to, trapezoidal, cylindrical (e.g., pen shaped), hemispherical, spherical, and rectangular. The differing shapes provide different refraction indexes, which are useful for analyzing different samples. Spherical ATR crystals reduce the beam diameter by a factor of two, thus, concentrating the beam to a smaller spot size. As a result, the beam exerts more pressure on the sample and allows for improved analysis of small samples.

The ATR crystal can be configured so that a beam of light enters the crystal, reflects off the interface, and exits the crystal. Such a crystal is known as a single bounce crystal. A single bounce crystal reduces Fresnel reflection losses due to the shorter path length of the beam. Because of the reduction of Fresnel reflection losses, the single bounce ATR improves both qualitative and quantitative analysis of strongly absorbing samples, e.g., aqueous liquids, organic liquids, pastes, and powdered solids.

Multiple bounce ATR crystals can also be used. These provide the advantage of attenuating the beam multiple times, thus, providing a higher sensitivity to smaller sample concentrations or the percentage of components within a sample. In certain embodiments, the ATR crystal can be coated in order to restrict pathlength (e.g., to reduce the number of bounces that will impinge the sample).

Detectors can include, but are not limited to, silicon detectors (PDA, CCD detectors, individual photo diodes), photomultiplier tubes, Ga detectors, InSb detectors, GaAs detectors, Ge detectors, PbS detectors, PbSi photoconductive photon detectors, PbSe photon detectors, InAs photon detectors, InGaAs photon detectors, photoconductive photon detectors, photovoltaic photon detectors, InSb photon detectors, photodiodes, photoconductive cells, CdS photoconductive cells, opto-semiconductors, or HgCdTe photoconductive detectors. A single detector or an array of detectors can be used. Preferably, the detector connects to a processing unit, which can convert the interferogram signal to a spectrum.

FT (Fourier Transform) Spectrometers, FTIR (Fourier Transform Infra-Red) Spectrometers, or Double-beam Spectrometers can also be used with the ATR crystal. These devices are configured in a conventional manner, except that instead of the beam of light impinging the sample, the beam of light impinges the ATR crystal in contact with the sample.

FIG. 1(a) illustrates a schematic side view of a preferred embodiment of the present invention, which includes an ATR crystal 76, a first connecting device 26, and a second connecting device 3. The first connecting device 26 transmits a beam 25 of light, which is generated by a radiation source 23, to the ATR crystal 76 in the side of a containment vessel 6. While traveling to the ATR crystal 76, the beam impinges a filter 30, which changes the beam 25 from polychromatic light to monochromatic light. The beam 25 enters the ATR crystal 76 at an interface 7 and while traveling through the ATR crystal 76 impinges an interface 15, located between the ATR crystal 76 and a substance 4, at least once. Each time the beam 25 contacts the interface 15 at or above a critical angle 44 (See FIGS. 4,5 ), an evanescent wave 16 is generated. The evanescent waves 16 penetrate the substance 4 and are attenuated in the regions of the spectrum where the substance 4 absorbs energy. The attenuated energy of each evanescent wave 16 is passed back to the beam 25. The beam 25 then exits the ATR crystal 76 at an interface 10 and is directed to a detector 18 by the second connecting device 3. The detector 18, which can be connected to a processing device 19, records the attenuated beam 25. The detected beam can then be processed by the processing device 19 to generate an absorbance spectrum of the dissolution medium. In certain embodiments, processing device 19 may subtract a baseline spectrum (the data obtained by using the present invention without a substance present) from a sample spectrum (the data obtained by using the present invention with a substance present) to obtain a baseline corrected absorption spectra.

As one of ordinary skill in the art will appreciate, the spectrum generated by the ATR crystal may be affected and deviate from the general linearity of the Beer-Lambert law by such chemical and instrumental factors including, but not limited to, deviations in the absorptivity coefficients at high concentrations of the sample due to electrostatic interactions between molecules in close proximity within the sample, the randomized scattering of the radiation beam due to particulates in the sample, any innate fluoresecence or phosphorescence of the sample, any shifts in chemical equilibria as a function of concentration in the sample, and stray light. These problems, however, can be avoided or compensated for using conventional techniques.

An aperture or opening is formed in the side of the containment vessel. The ATR crystal 76 is secured to the side of the containment vessel 6, covering the aperture, such that one side of the ATR crystal forms a portion of the interior surface of the vessel. The ATR crystal can be secured to the containment vessel in any suitable manner, including, for example, with a fastener, gasket, or adhesive (such as silicone adhesives). In this way, the ATR crystal is embedded in the containment vessel.

A cover 5 can be placed over the containment vessel, so as to prevent loss, e.g., through evaporation, of the substance 4.

The equations $N = L \cot F/2t$ and $D_p = w/2\pi n_c [\sin^2 F - (n_s/n_c)^2]^{1/2}$ (where N is the number of reflections in the ATR crystal 76, L is the length of the ATR crystal 76, F is the angle of incidence, t is the thickness of the ATR crystal 76, $D_p$ is the depth of penetration of the evanescent wave 16, $n_c$ is the refractive index of the ATR crystal 76, $n_s$ is the refractive index of the substance 4, and w is the wavelength of the light) determine the number of reflections of the beam 25 within the ATR crystal 76 and the depth of penetration of the beam 25 into the sample 4. The effective pathlength of the beam 25 may then be determined by $P = N \times D_p$ (where N is the number of reflections and $D_p$ is the depth of penetration). The effective pathlength gives a measure of the intensity of the resulting spectrum.

The filter 30 can be a monochromator, a spectrograph, a linear variable filter, a bandpass filter, or an interference filter. The filter 30 can also be a monochromator-filter type device, rotating tilting filter wheel, spinning filter wheel, AOTF(Acousto Optic Tunable Filter), or pre-dispersive grating monochromator.

Figure 1B:
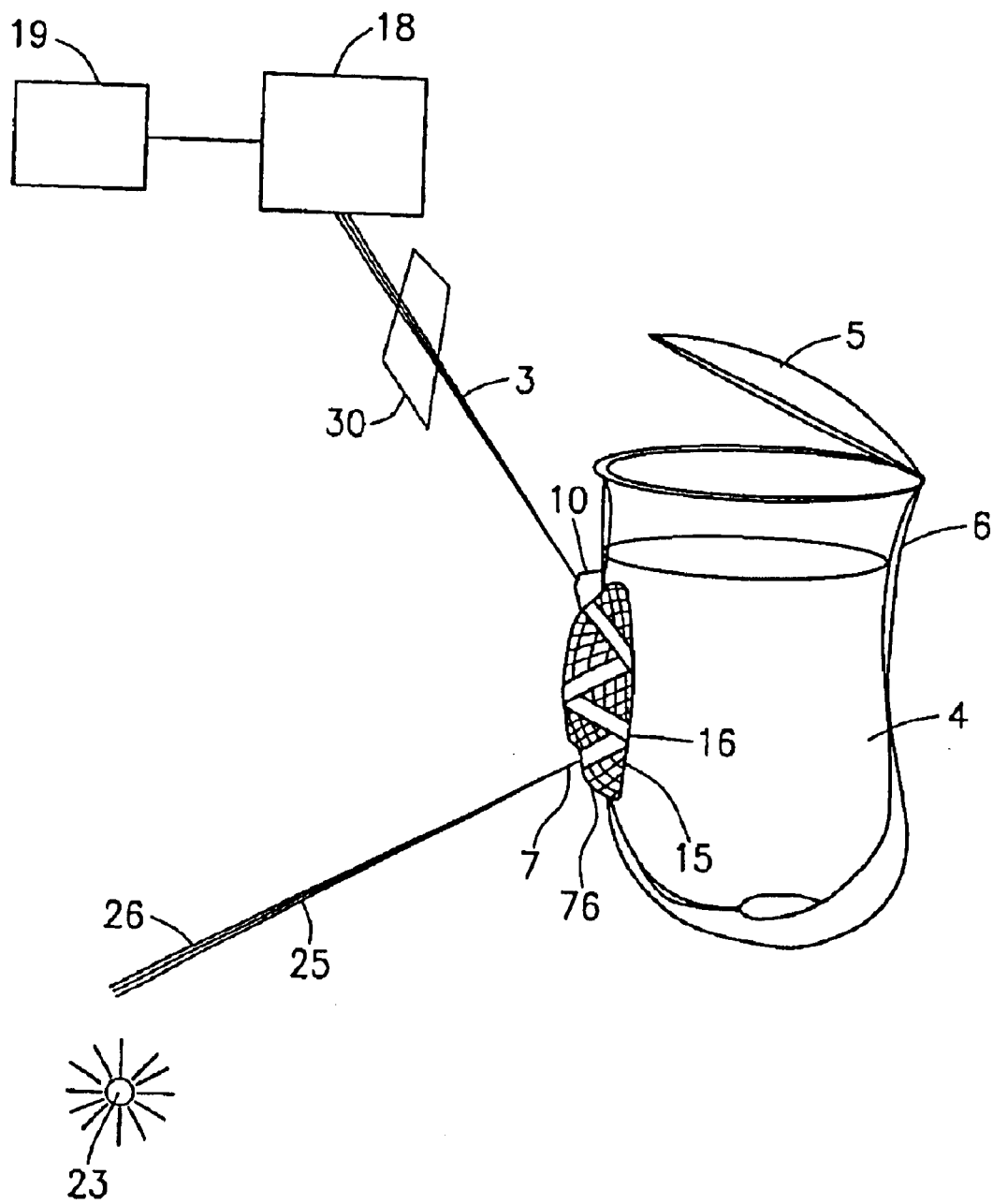

Although the filter 30 is located between the radiation source 23 and the ATR crystal 76 in FIG. 1(a), the filter 30 can be located between the ATR crystal 76 and the detector 18, as shown in FIG. 1 (b), with similar components bearing identical reference numbers to FIG. 1(a). However, if the filter 30 is between the ATR crystal 76 and the detector 18, the filter can not be a pre-dispersive grating monochromator, but can be a post-dispersive grating monochromator.

The radiation source 23 can be a QTH lamp, a deuterium lamp, a set of light emitting diodes, or a laser. The radiation source 23 can also be a Xenon Lamp, a Mercury Xenon Lamp, a Xenon Flash Lamp, a Metal Halide Lamp, a GaAs Infrared LED, a GaAlA Infrared LED, GaAlA Infrared LED, or a GaAAs Infrared LED (all produced by Hamamatsu Corporation). If a laser, LED, or other monochromatic light source is used, there is no need for a filter 30, either before, or after, the ATR crystal.

The embedded ATR crystal 76 may be composed of ZnSe, Ge, SeAs, Cds, CdTe, CsI, InSb, Si, Sapphire ($Al_2O_3$), diamond Anneled Glass, borosilicate crown glass, BK7 Anneled Glass, UBK7 Annealed Glass, LaSF N9 Anneled Glass, BaK1 Annealed Glass, SF11 Annealed Glass, SK11 Annealed Glass, SF5 Annealed Glass, Flint Glass, F2 Glass, Optical Crown Glass, Low-Expansion Borosilicate Glass (LEBG), Pyrex, Synthetic Fused Silica (amorphous silicon dioxide), Optical Quality Synthetic Fused Silica, UV Grade Synthetic Fused Silica, ZERODUR, AgBr, AgCl, KRS-5 (a TlBr and TlCl compound), KRS-6 (a TlBr and TlCl compound), ZnS, $ZrO_2$, AMTIR, or diamond. Movements for UV/NVIS applications, other crystals, such as Fused Silica can be used.

Although toxic, the Zinc Selenide (ZnSe) crystal, which is clear and has a polycrystalline lattice-work with a grain size of approximately 70 $\mu$m, is essentially free of extrinsic impurity absorptions, and thus provides extremely low bulk losses from scatter. Moreover, the ZnSe crystal has a wide spectroscopic range of about 20,000–500 $cm^{-1}$, transmits in the range of about 0.5 $\mu$m to about 15 $\mu$m, and has a refractive index of about 2.43.

As an optical element, the ZnS crystal, which has a refractive index of about 2.25, has a spectroscopic range of about 50,000–770 $cm^{-1}$ and functions in wet or aqueous solutions, but does not function in acidic solutions.

Si crystals, which have a higher refractive index than KRS-5 and ZnSe crystals, are suitable for applications involving wet samples and aqueous solutions, even acids and alkalis, however, HF and $HNO_3$ attack the crystal. Spectroscopic range is about 4000–1500 $cm^{-1}$ and in the far IR about 400–30 $cm^{-1}$. The refractive index of the crystal is about 3.42.

Germanium optical elements with a refractive index of about 4.01 have the highest refractive index of common IR materials. Due to a wide transmission range covering 1.8÷÷17 $\mu$m, spectroscopic range of about 5000–550 $cm^{-1}$, and opacity in visible ranges, Germanium crystals are useful for analyzing hard polymers and carbon filled samples. The Germanium optical element is suitable for wet samples and aqueous solutions, even acids and alkalis. However, the Geranium optical element is attacked by hot sulphuric acids and aqua regia, and is subject to thermal shock.

KRS-5 is a general purpose crystal for may experiments, however, the crystal is not well suited for applications involving wet or aqueous solution and can be distorted by pressure. Moreover, the KRS-5 crystal is extremely toxic. The crystal has a refractive index of about 2.38 and a spectroscopic range of the crystal is about 17,000-250 $cm^{-1}$.

AMTIR (Amorphous Material which Transmits Infrared Radiation) is a chalcogenide glass with a refractive index of about 2.5. The AMTIR crystal, which has a spectroscopic range of about 4000–725 $cm^{-1}$, is suitable for acidic solutions involving wet samples or aqueous solutions, but the crystal is attacked by bases.

Diamond crystals, which have a spectroscopic range of about 4000–400 $cm^{-1}$ and a type 2A absorption band in the 2500–2000 $cm^{-1}$ region, are suitable for applications involving aqueous solutions from pH 1 to 14. Furthermore, the durability of the diamond allows contact efficiencies approaching 100%. The refractive index of the diamond crystal is about 2.35. A bullet shaped focusing crystal, made from ZnSe or KRS-5, can be placed in optical contact with the diamond crystal, so as to provide interfacing optics for the input and output radiation.

The entire ATR crystal 76 or a portion thereof, e.g., the side that reflects the beam of light onto the interface 15, can be coated with a metallic coating, dielectric coating, bare aluminum, protected aluminum, enhanced aluminum, UV-enhanced aluminum, internal silver, protected silver, bare gold, protected gold, MAXBRIte, Extended MAXBRIte, Diode Laser MAXBRIte, UV MAXBRIte, or Laser Line MAXR. The coating increases the amount of light reflected, thus, improving the accuracy of the data. Furthermore, the coating can be a material that only reflects (or allows transmittance) of specific wavelengths of light. In this manner, the coating can be arranged on the ATR crystal 76 so that only specific wavelengths of light reach the sample.

The ATR crystal 76 can be trapezoidal, cylindrical, hemispherical, spherical, or rectangular. The differing shapes affect the refraction index and the number of times the beam 25 reflects while in the ATR crystal 76.

Single bounce crystals, i.e., the beam enters the crystal, reflects off the interface, and exits the crystal, reduce Fresnel reflection losses due to the shorter path length of the beam 25. Fresnel reflection losses result from diffraction which involves spherical waves incident upon an obstruction, effectively originating from a point Because of the reduction of Fresnel reflection losses, the single bounce crystal improves both qualitative and quantitative analysis of strongly absorbing samples, e.g., aqueous liquids, organic liquids, pastes, and powdered solids.

Spherical crystals, as described by Nicolet Instrument Corp., reduce the beam 25 diameter by a factor of two, resulting in a concentration of energy to a smaller spot size. As such, the beam 25 exerts more pressure on the substance 4 and allows for improved analysis of small samples.

The first and second connecting devices 26,3 can be hollow, rigid tube wave guides (the "light-pipe," W. M. Doyle and N. A. Jennings, Spectroscopy 5, (1) 34–38 (1990)). However, the tubes are fairly inflexible, requiring careful mechanical design dictated by the geometry of the reaction vessel being used, and thus do not lend themselves to repeated use in environments where the reaction vessel dimensions and/or shape may vary. Furthermore, since rigid tube wave guides depend upon carefully aligned mirrors to transmit the signal around bends or corners in the tube, the rigid tube wave guides are extremely sensitive to vibration, making the wave guides unsuitable for use in typical industrial environments.

The first and second connecting devices 26,3 can also be flexible fiber optic cable, which may contain one or more optical fibers that transmit radiation in the appropriate part of the electromagnetic spectrum. Fiber optic cables can be used in a wide variety of environments because of their durability and malleability. For example, cables for use in the visible region of the spectrum can be made using fibers of silica glass.

The first and second connecting devices 26,3 can be constructed of, but are not limited to, Optical Glass, Fused Silica Fiber, low OH Fused Silica Fiber, Fluoride, or Chalcogenide fiber. High quality optical glass transmits wavelengths from about 400 nm to about 900 nm. However, transmission in the UV range is very low and wavelengths below about 350 nm are not transmitted. When the application requires UV light, more expensive Fused Silica fibers can be used. At about 1.4 microns, all fibers except those specifically designed for IR transmission show a significant drop in transmission because of absorption in the glass. Low OH Fused Silica Fibers specifically designed for the NIR do not show the transmission drop at about 1.4 microns and transmit well between about 0.4 microns and about 2.5 microns. Fluoride and Chalcogenide Fibers can cover a range form about 1 micron to about 10 microns.

The containment vessel 6 can be constructed of an inert material, e.g., Teflon, fluoroplastic, PTFE, NALGENE, lead, stainless steel, or Teflon fluoropolymer resin. Alternatively, the vessel 6 could be made of glass, PYREX, crown, Fused Silica borosilicate glass, or Flint.

A wide variety of detectors 18 can be used, including, but not limited to, silicon detectors (PDA, CCD detectors, individual photo diodes), photomultiplier tubes, Ga detectors, InSb detectors, GaAs detectors, Ge detectors, PbS detectors, PbSi photoconductive photon detectors, PbSe photon detectors, InAs photon detectors, InGaAs photon detectors, photoconductive photon detectors, photovoltaic photon detectors, InSb photon detectors, photodiodes, photoconductive cells, CdS photoconductive cells, optosemiconductors, or HgCdTe photoconductive detectors. The detector 18 can consist of one element (i.e., one detector unit) or of a plurality of elements organized into an array.

Figure 2:
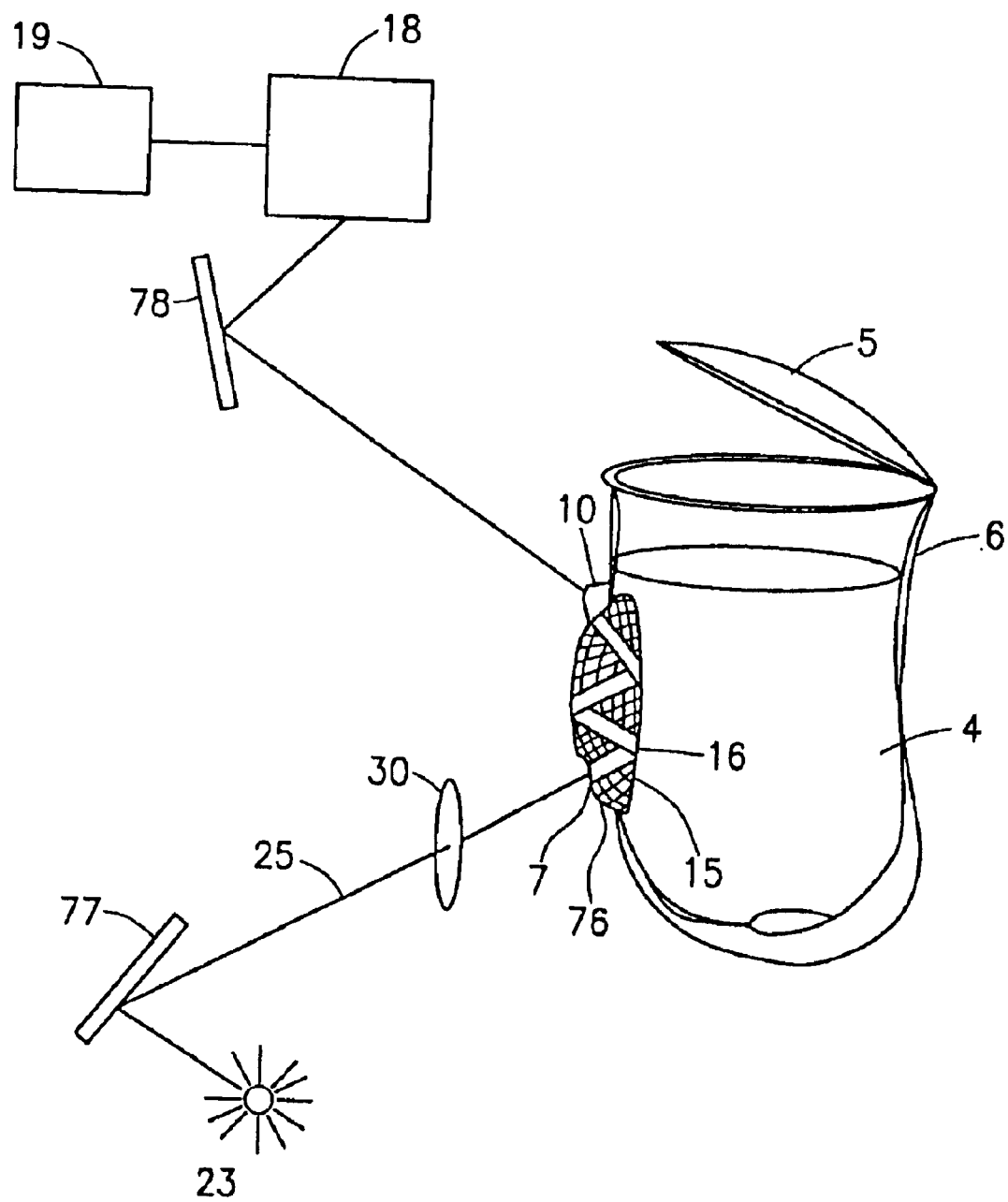
FIG. 2 illustrates a schematic side view of the present invention having a first a first mirror and a second mirror in place of the first connecting device and the second connecting device.

FIG. 2 illustrates a schematic side view the present invention having a first a first mirror 77 and a second mirror 78 in place of the first connecting device 26 and the second connecting device 3 (FIG. 1). The first mirror 77 reflects the beam 25 of light, which is generated by the radiation source 23, to the ATR crystal 76. In route to the ATR crystal 76, the beam impinges the filter 30, which changes the beam of light from polychromatic light to monochromatic light. The beam 25 enters the ATR crystal 76 and while traveling through the ATR crystal 76 impinges an interface 15, located between the ATR crystal 76 and a substance 4, at least once. Each time the beam 25 contacts the interface 15 at or above the critical angle 44 (See FIGS. 3, 4), an evanescent wave 16 is generated. The evanescent waves 16 penetrate the substance 4 and are attenuated in the regions of the spectrum where the substance 4 absorbs energy. The attenuated energy of each evanescent wave 16 is passed back to the beam 25. The beam 25 then exits the ATR crystal 76 and is directed to the detector 18 by the second mirror 78. The detector 18, which is connected to the processing device 19, records the attenuated beam 25 and the detected beam is then processed in the manner described above to generate a spectrum of the dissolution medium. Alternatively, the filter 30 can be placed between the ATR crystal 76 and the detector 18 instead of between the ATR crystal 76 and the radiation source 23.

Figure 3A:
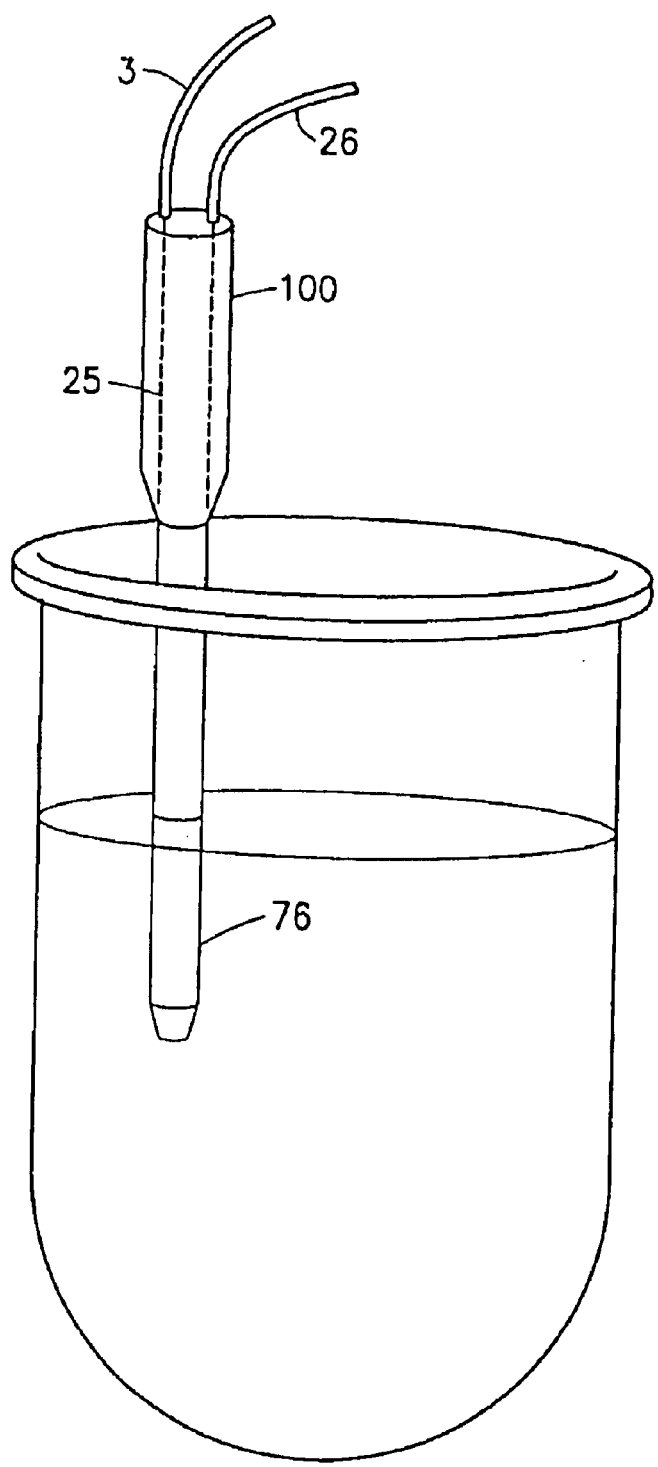
FIGS. 3(a,b) illustrates another embodiment of the present invention, which shows the ATR crystal mounted on a probe.

FIG. 3(a) illustrates an alternate embodiment of the present invention, which shows the ATR crystal 76 mounted on a probe 100. Components 18, 19, 30, 77, 78 and 23 (not shown) can be configured in the same manner as described above with reference to FIGS. 1 and 2. The probe 100 is inserted into the containment vessel 6 through an aperture. If desired, the probe 100 can be shaped so that a seal is formed with the containment vessel 6, thereby, preventing loss of the substance 4 by evaporation. The radiation source (not shown) generates the beam of light. The beam of light passes through the filter (not shown) and enters the first connecting device 26. The first connecting device 26 then transmits the beam 25 to the probe 100. The probe 100, in turn, transmits the beam to the ATR crystal 76. The beam 25 then enters the ATR crystal 76 and travels through the ATR crystal 76. While traveling through the ATR crystal 76, the beam 25 impinges the interface 15 between the ATR crystal 76 and the substance 4 at least once and in so doing generates the at least one evanescent wave. The evanescent wave penetrates the substance 4 and is attenuated in the regions of the spectrum where the substance 4 absorbs energy. The attenuated energy of the evanescent wave is passed back to the beam 25, which then exits the ATR crystal 76 and re-enters the probe 100. The probe 100 transmits the beam 25 to the second connecting device 3. The second connecting device 3 then directs the bean to the detector (not shown). The detector, which can be connected to the processing device (not shown), records the attenuated light beam and the detected beam is then processed to generate a spectrum report of the dissolution medium.

Figure 3B:
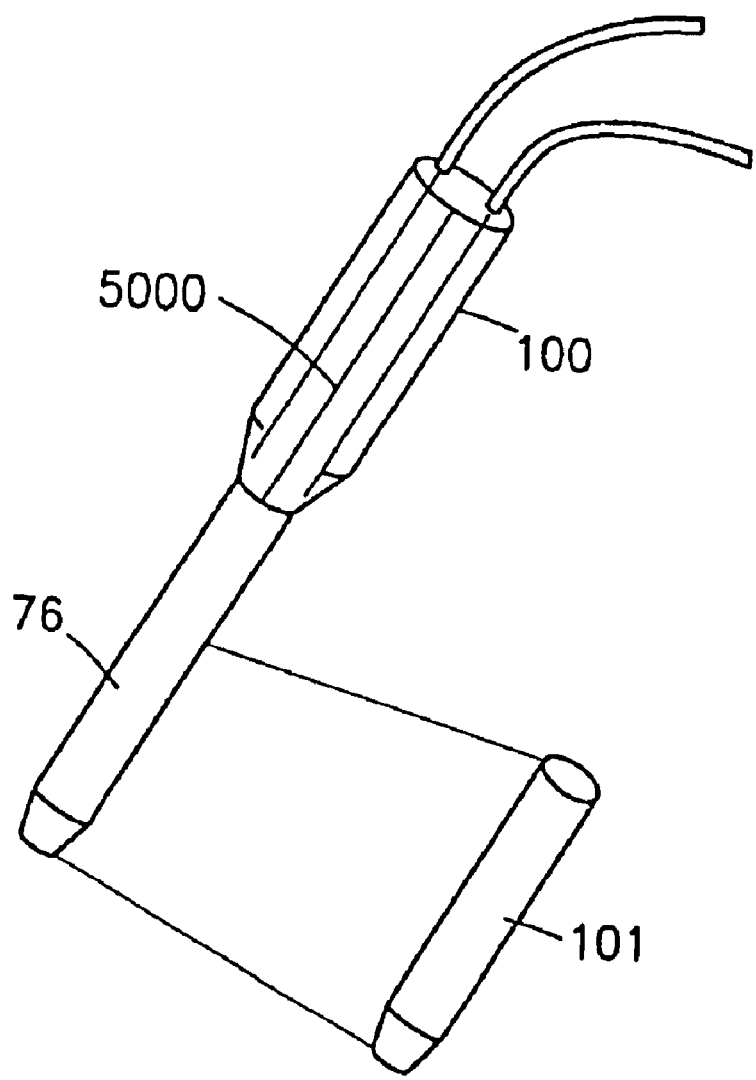

FIG. 3(b) illustrates a side view of the probe 100. A probe cover 101 is also shown. The probe cover 101 can selectively cover the outer surface of the ATR crystal 76, so that absorbance contacts with the substance 4 are decreased.

In order to prevent interference between the portion of the beam 25 exiting the ATR crystal 76 and the portion of the beam 25 entering the ATR crystal 76, a partition 5000 may be placed in the middle of the probe 100. Also, the first and second connecting devices 26,3 can also (or alternatively) be connected to the probe 100 in such a way that there is a direct connection between the output of the first connecting 26 and the input of the ATR crystal 76, and a direct connection between the output of the ATR crystal 76 and the input of the second connecting device 3.

The probe 100 can be constructed of chalcogenide fiber, e.g., from glass composed of arsenic, selenium, and tellurium (AsSeTe glass). Chalcogenide fiber performs well in the mid-IR range, transmitting across a substantial part of the mid-IR region, namely 900–5000 cm. The probe 100 can also be clad with a glass of lower refractive index to prevent escape or "leakage" of radiation from the fiber.

Alternatively, the probe 100 can be constructed of an inert material, e.g., Teflon, fluoroplastic, PTFE, NALGENE, or Teflon fluoropolymer resin, and contain a plurality of internal connecting devices 105, e.g., fiber optic cables, as shown in FIG. 3(b). To transfer the light from the first connection device 26 to the ATR crystal 76, a first set of the internal connecting devices 105 is attached to the output of the first connecting device 26 and input of the ATR crystal 76. To transfer the light from the output of the ATR crystal 76 to the input of the second connecting device 3, a second set of the internal connecting devices 105 is attached to the input of the second connecting device 3 and the output of the ATR crystal 76. Preferably, the internal connection devices 105 are connected to the first and second connecting devices 26,3 and the ATR crystal 76, so as to transmit the beam of light 25 to and from the ATR crystal 76.

Instead of internal connecting devices 105, the first and second connecting devices 26,3 can be embedded inside the probe 100, with the output of the first connecting device 26 connected to the input of the ATR crystal 76, and with the input of the second connecting device 3 connected to the output of the ATR crystal 76.

Figure 4:
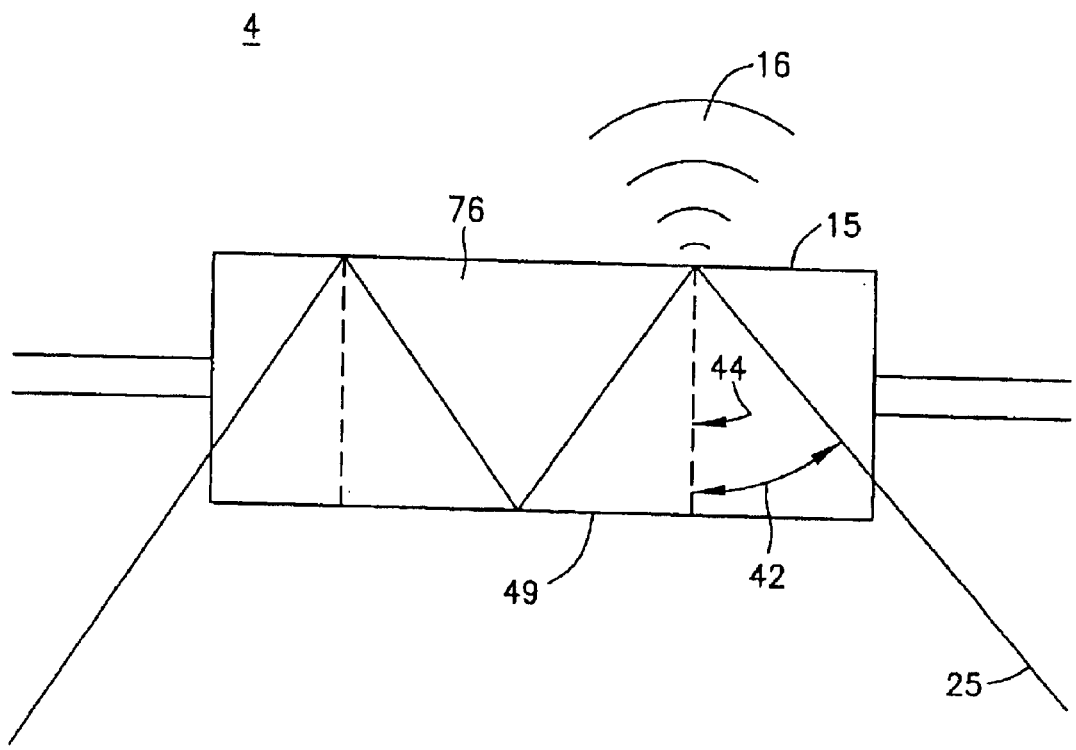
FIG. 4 illustrates a multiple bounce embodiment of the ATR crystal.

FIG. 4 illustrates a multiple bounce embodiment of the ATR crystal 76. The beam 25 of light enters the ATR crystal 76 at an angle of incidence 42 and reflects off the interface 15 of the ATR crystal 76 and the substance 4. The beam then reflects off the opposing side 49 of the ATR crystal 76, which can be coated with a material to enhance reflectiveness, and returns to the interface 15 a second time. Each time the beam reflects off the interface 15, the beam does so at the angle of incidence 42. If the angle of incidence 42 equals or is greater than the critical angle 44, the incident light undergoes total internal reflection and the evanescent wave 16 is generated. Snell's Law determines the critical angle 44: $\sin_{crit}=\sin^{-1} n_2/n_1$ (where $n_1$ is the index of refraction of the ATR crystal 76 and $n_2$ is the index of refraction for the substance 4). In regions of the spectrum where the substance 4 absorbs energy, the evanescent wave 16 is attenuated, and the attenuated energy passed back to the beam 25. After impinging the interface 15 the second time, the beam 25 exits the ATR crystal 76. Any spectral data derived from the interface 15 can be masked out by subtracting the spectral data from the detector 18 from spectral data generated by an empty vessel. Alternatively, a material can be placed at the opposing interface 49 that does not absorb radiation in the wavelength band of the light transmitted through the crystal.

The refractive index of the ATR crystal 76, the refractive index of the substance 4, and the angle of incidence 42 affect the depth of penetration. For example, reducing the angle of incidence 42 or using a crystal with a lower refractive index increases the depth of penetration of the evanescent wave 16, however, at shallow depths of penetration, the evanescent wave 16 generally provides more reliable results.

Figure 5:
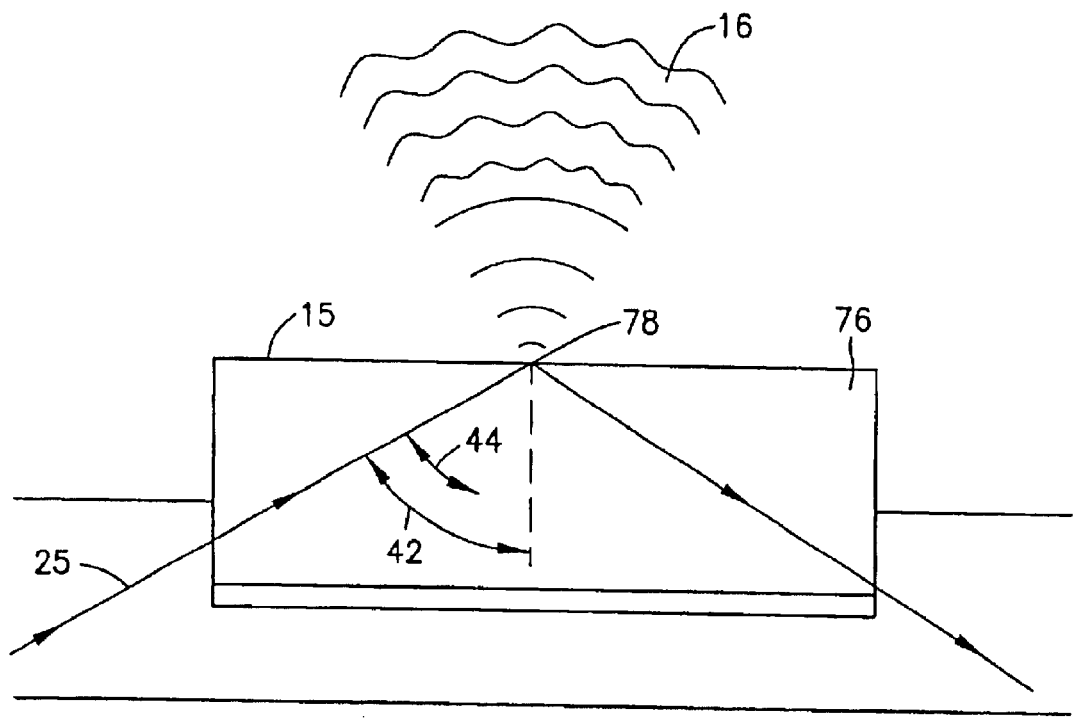
FIG. 5 illustrates a single bounce embodiment of the ATR crystal.

FIG. 5 illustrates a single bounce embodiment of the ATR crystal 76. The beam 25 enters the ATR crystal 76 at the angle of incidence 42 and reflects off the interface 15 at a reflection point 78. If the angle of incidence 42 at which the beam contacts the interface 15 equals or is greater than the critical angle 44, the incident light undergoes total internal reflection and the evanescent wave 16 is generated. Snell's Law determines the critical angle 44: $\sin_{crit}=\sin^{-1} n_2/n_1$ (where $n_1$ is the index of refraction of the ATR crystal 76 and $n_2$ is the index of refraction for the substance 4). In regions of the spectrum where the substance 4 absorbs energy, the evanescent wave 16 is attenuated, and the attenuated energy passed back to the beam 25. The beam 25 then exits the ATR crystal 76.

Figure 6:
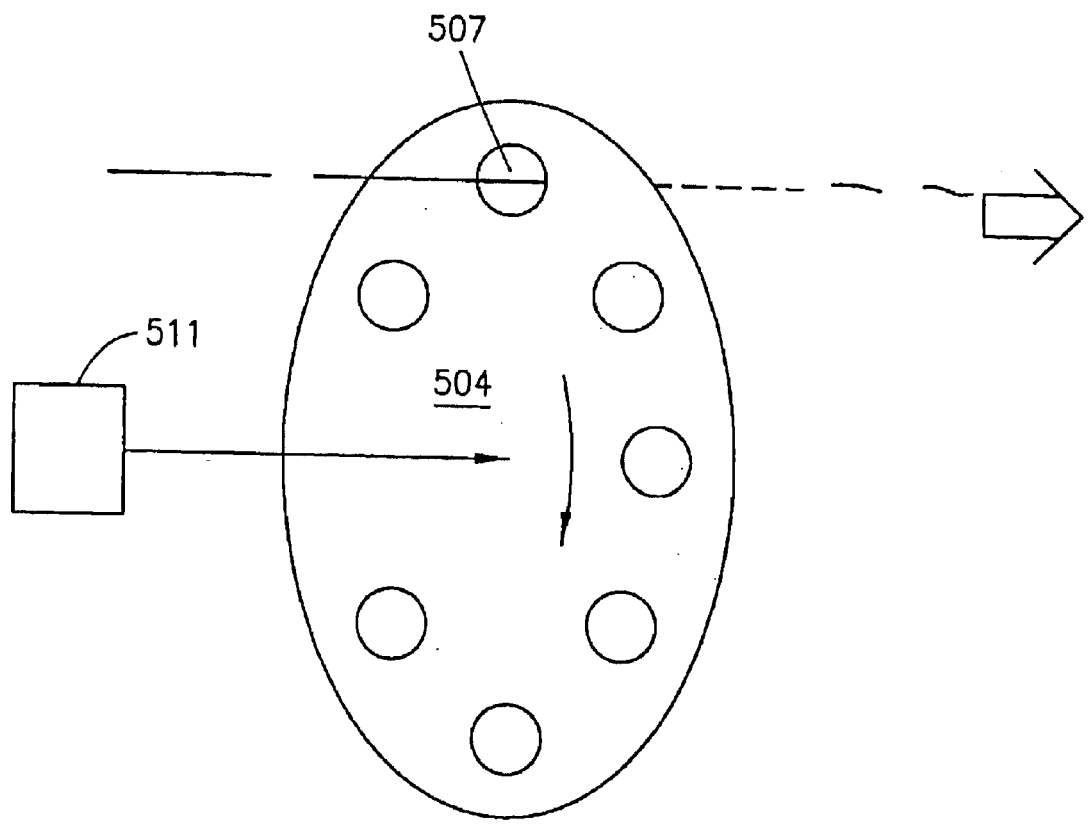
FIG. 6 shows a monochromatic filter-type device.

FIG. 6 shows a monochromatic filter-type device. A beam of light impinges a rotating circular disk 504, which includes a plurality of narrow bandpass optical filters 507. The disk can be rotated so that the beam of light passes through each of the narrow bandpass optical filters 507. An encoder 511 controls which optical filter 507 is presently under the light source. The optical filters 507 filter the beam of light so that only a narrow selected wavelength range passes through. The monochromatic filter-type device can be used as the filter 30 in any of the devices described in FIGS. 1–3, upstream or downstream of the ATR crystal 76.

Figure 7:
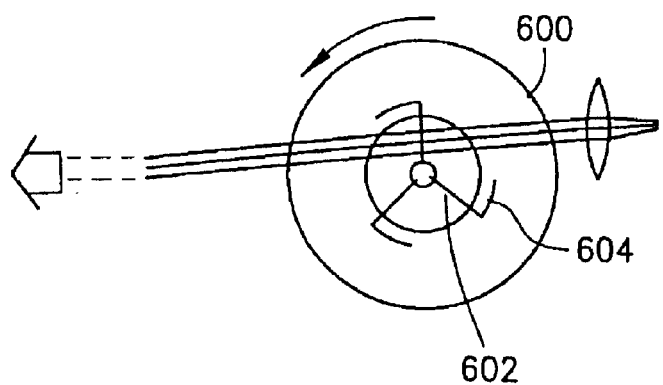
FIG. 7 shows a rotating tilting filter wheel utilizing wedge interference filters having a light blocking flag.
Figure 8:
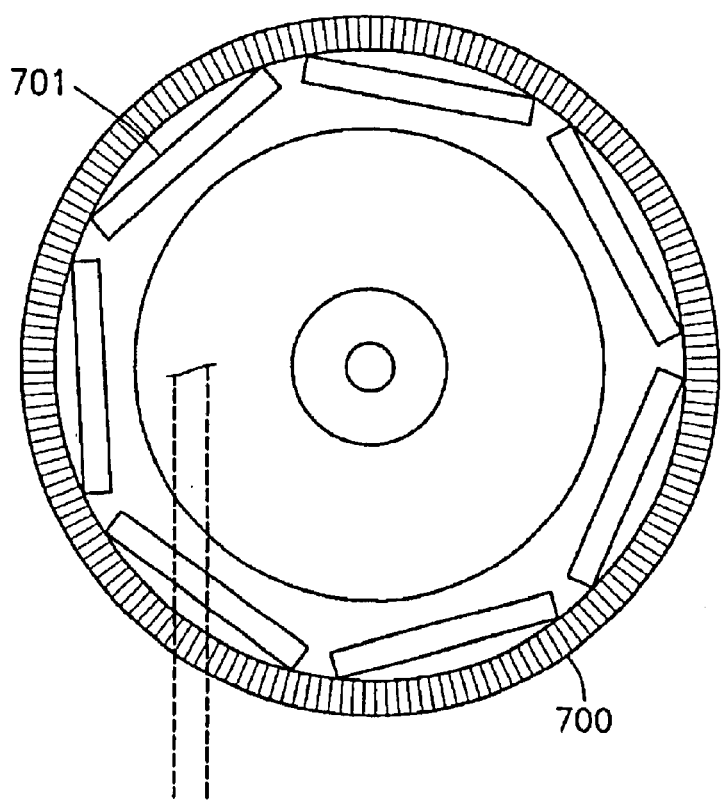
FIG. 8 shows a spinning filter system in which the light passes through an encoder wheel.

FIGS. 7 and 8 illustrate two basic forms of filter-type NIR devices utilizing a tilting filter concept.

FIG. 7 shows a rotating tilting filter wheel utilizing wedge interference filters having a light blocking flag 604. Light is transmitted through a filter wheel 600 at varying wavelengths and bandpasses, which are dependent on the incident angle of the light passing through the interference filter wedge 602. The rotating filter wheel can be used as the filter 30 in any of the devices as described in FIGS. 1–3, upstream or downstream of the ATR crystal 76.

FIG. 8 shows a spinning filter wheel in which the light passes through an encoder wheel 700, having a plurality of interference filters 701. The spinning filter wheel operates using the same basic principle as the tilting filter of FIG. 7, but the interference filters 701 of the spinning filter wheel are mounted in the encoder wheel 700 for greater positioning accuracy (wavelength reproducibility) and greater reliability. The spinning filter wheel can be used as the filter 30 in any of the devices as described in FIGS. 1–3, upstream or downstream of the ATR crystal 76.

Figure 9:
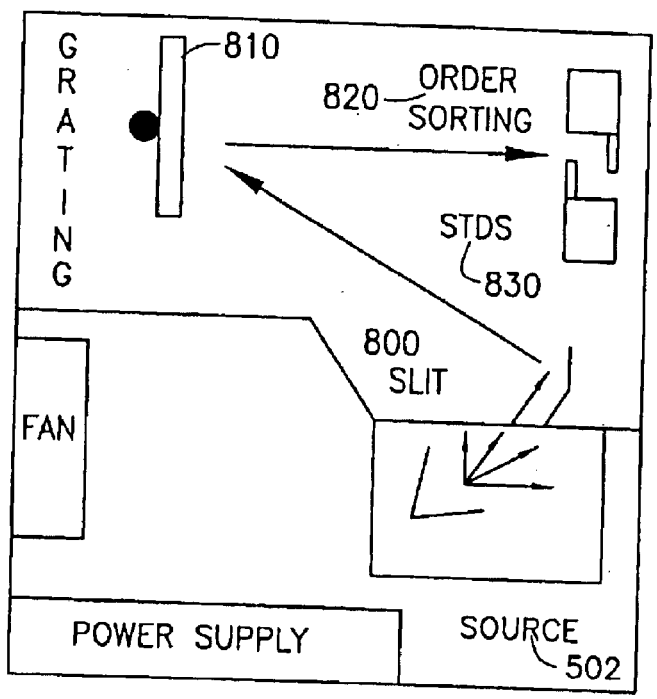
FIG. 9 shows a typical pre-dispersive monochromator-based instrument, where the light is dispersed prior to striking the sample.

FIG. 9 shows a typical pre-dispersive monochromator-based instrument, where the light is dispersed prior to striking the sample. The beam of light passes through an entrance slit 800 and onto a grating 810. The grating 810 separates the light into a plurality of beams of different wavelengths. Via the order sorting 820 (to eliminate undesired wavelengths) and stds 830 (to provide a wavelength standard for calibration) components, a desired band of wavelengths is selected for transmission. The device may also be used as the filter 30 with any one of the embodiments of the present invention described above in FIGS. 1(*b*), 2, or 3, provided that it is located upstream of the ATR crystal 76.

Figure 10:
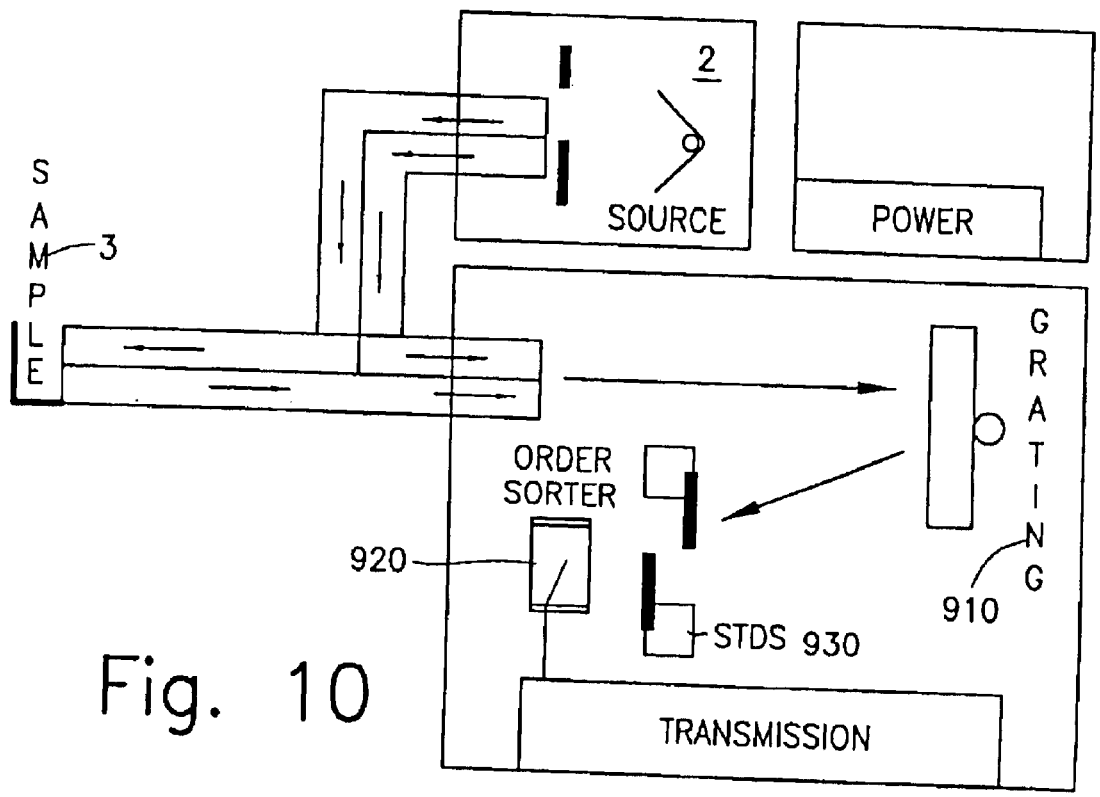
FIG. 10 shows a typical post-dispersive monochromator using the ATR crystal.

FIG. 10 shows a typical post-dispersive monochromator. This type of instrument provides the advantage of allowing the transmission of more energy on the sample. After the beam of light has exited the ATR crystal 76 (FIGS. 1–5), where the beam of light was attenuated, the light is reflected back to a grating 910 (the dispersive element). On striking the grating 910, the light is separated into the various wavelengths. An order sorting 920 (to eliminate undesired wavelengths) and an stds 930 (to provide a wavelength standard for calibration) component provide the desired band of wavelengths selected for transmission. As illustrated, this filter may be used as the filter 30 in with any one of the embodiments of the present invention described above in FIGS. 1(*b*), 2 or 3, provided that it is located downstream of the ATR crystal 76.

Figure 11:
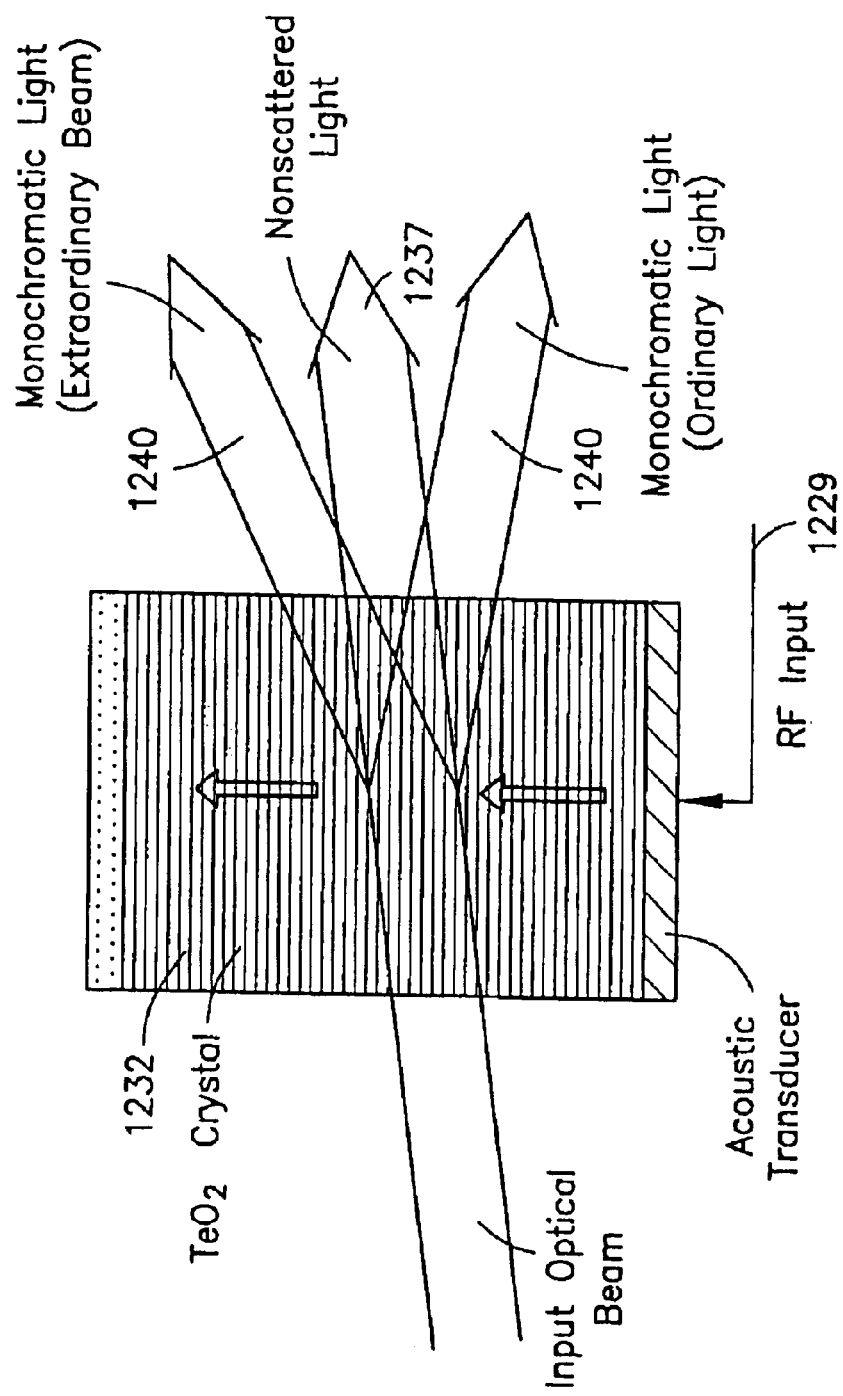
FIG. 11 depicts an Acousto Optic Tunable Filter spectrometer utilizing an RF signal to generate acoustic waves in a $TeO_2$ crystal.

FIG. 11 depicts an Acousto Optic Tunable Filter spectrometer utilizing an RF signal 1229 to generate acoustic waves in a TeO$_2$ crystal 1232. The beam of light transmits through the crystal 1232, and the crystal 1232 splits the beam of light into three beams: a center beam of unaltered white light 1237 and two beams of monochromatic and orthogonally polarized light 1240. The wavelength of the monochromatic light can be incremented across a wavelength band of interest by varying the RF frequency. One of the two beams of monochromatic light 1240 then pass to any of the devices described in FIGS. 1–3.

Figure 12:
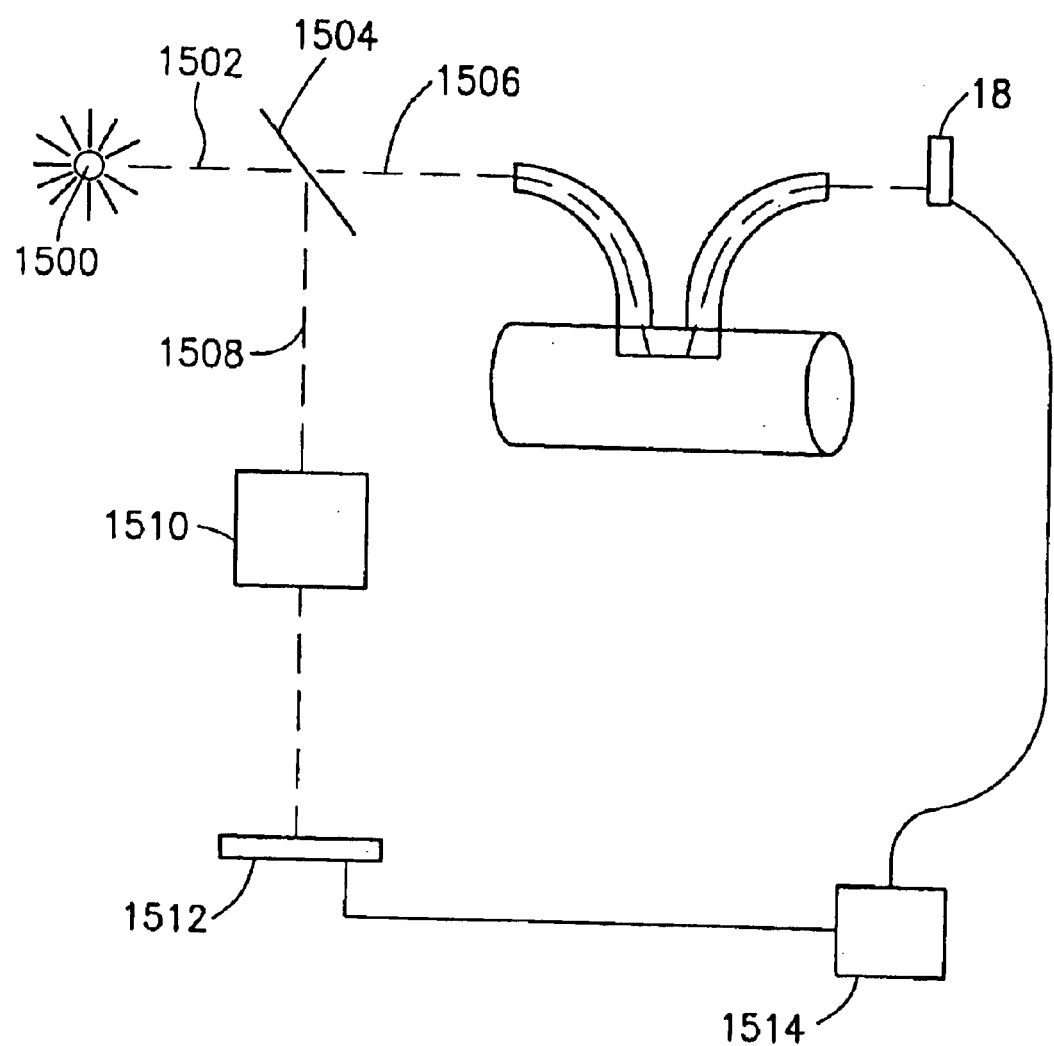
FIG. 12 depicts a Fourier Transform device.

FIG. 12 depicts a Fourier Transform device. A light emitting source 1500, e.g., an IR diode, produces a beam 1502. The beam 1502 impinges a beam splitter 1504, which splits the beam 1502 into a first half 1508 and a second half 1506 and in so doing sends the first half 1508 and second half 1506 in two directions at right angles. The first half 1508 continues to a stationary mirror 1590 and then back to the beam splitter 1504. The second half 1506 impinges a moving mirror 1510 and returns to the beam splitter 1504. The moving mirror 1510 changes the total path length of the second half 1506, so that when the first half 1504 and second half 1506 recombine to form a recombined beam 1512, the difference in path length creates constructive and destructive interference: an interferogram. The recombined beam 1512 passes into any of the devices described in FIGS. 1–3. A Fourier transform converts the data obtained from the detector 18 of the devices of FIGS. 1–3 to an intensity vs. time spectrum, and since time is the reciprocal of frequency, the spectrum can be converted into an intensity vs. frequency spectrum.

Figure 13:
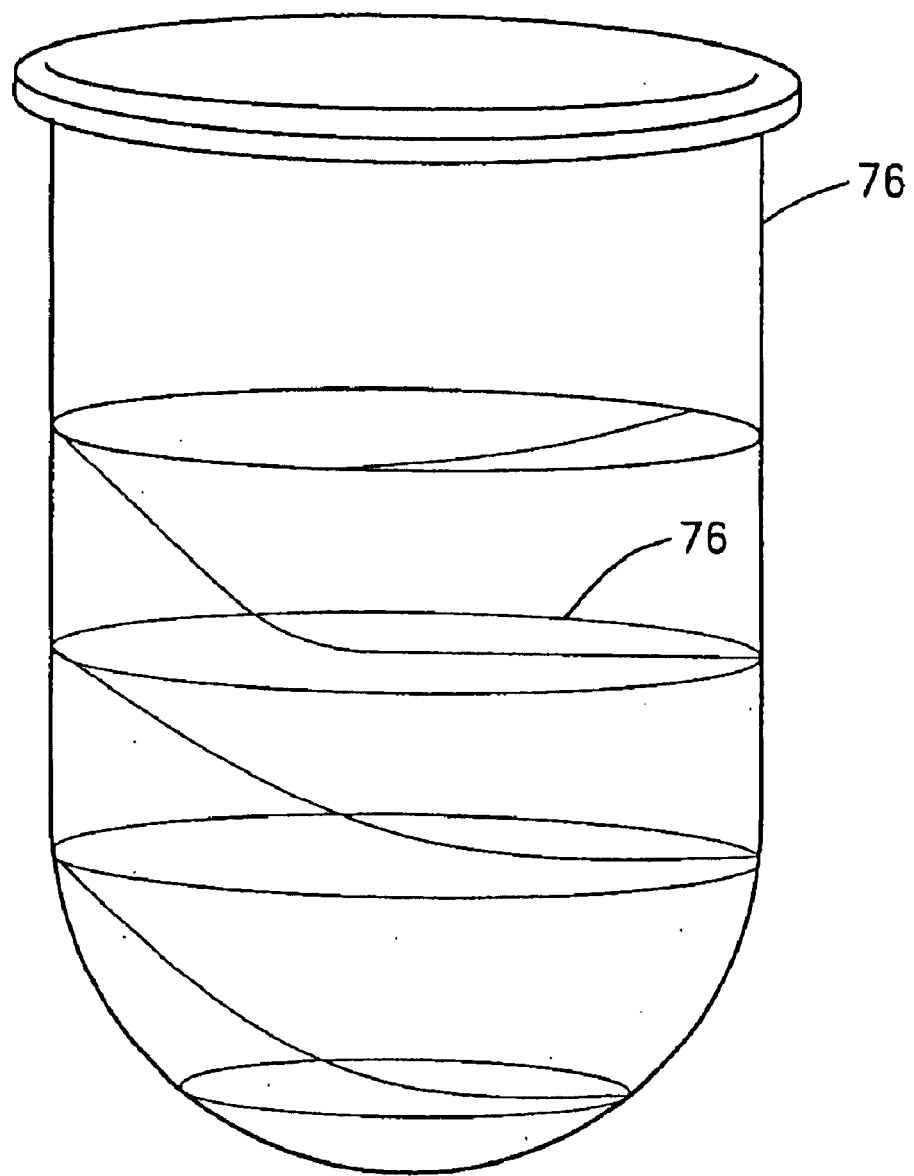
FIG. 13 shows another embodiment of the present invention, wherein an ATR crystal is disposed in a double helix along an inner surface of a vessel.

FIG. 13 schematically illustrates a side view of a preferred embodiment of the present invention, which includes a spiral ATR crystal 76. The ATR crystal 76, which can be composed of fused silica, is disposed along the inner surface of the vessel 6 in a double helix configuration. The double helix configuration spirals downward until it reaches the bottom of the vessel 6, and then spirals upward. This architecture allows a large number of bounces which are distributed throughout the interior surface of the vessel.

Figure 14:
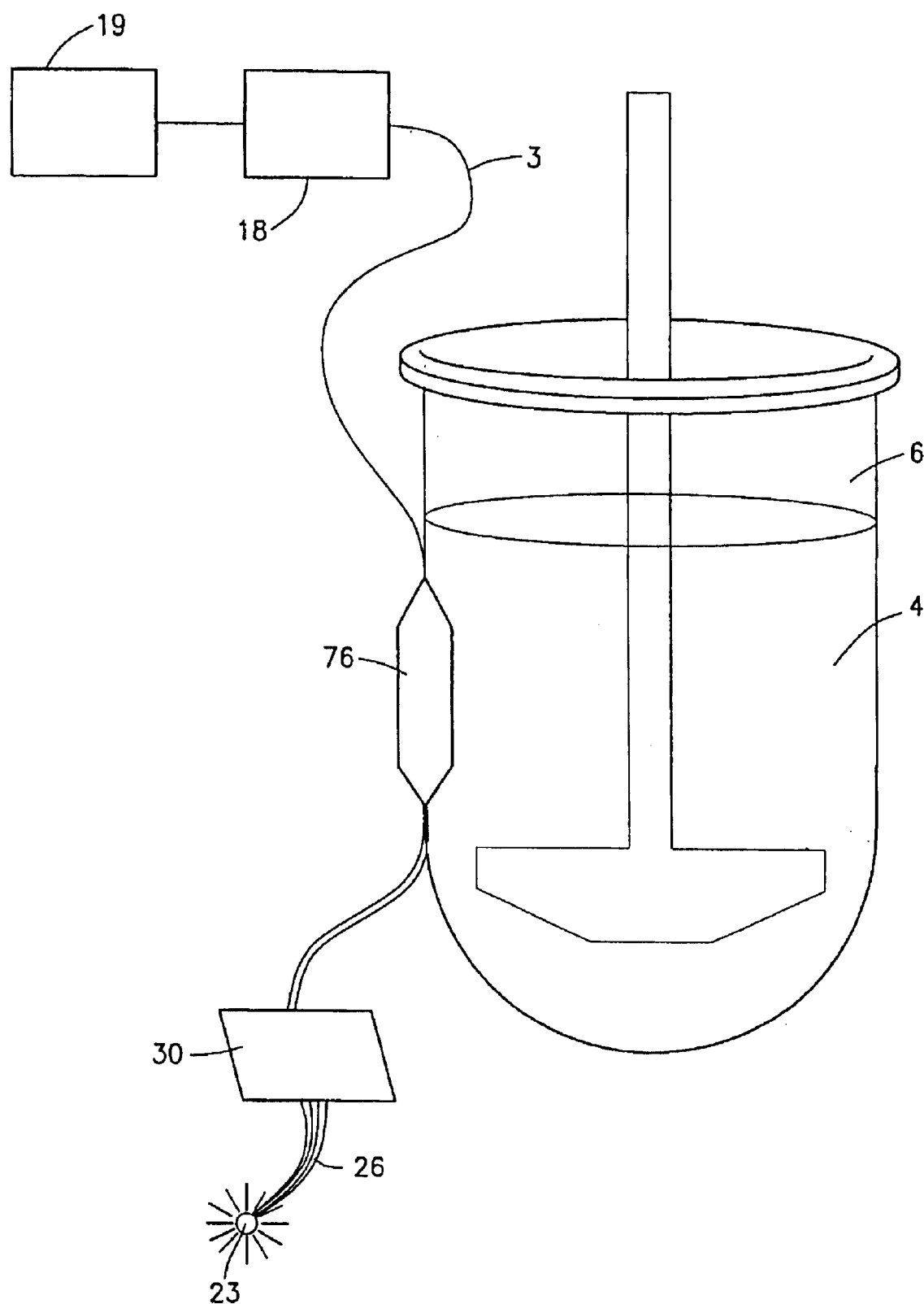
FIG. 14 shows an embodiment of the present invention which includes an ATR crystal embedded in a dissolution vessel.

FIG. 14 schematically illustrates a side view of a preferred embodiment of the present invention for performing dissolution testing of a dosage form. The processing device 19, detector 18, first connecting device 26, second connecting device 3, filter 30, ATR crystal 76, radiation source 23, vessel 6, and substance 4 are configured in the same manner described above with regard to FIG. 1(*b*). The arrangements shown in FIGS. 1(*b*) and 2 can similarly be used in conjunction with this embodiment. Also shown in FIG. 14 is a mixing shaft and paddle 10000 which conform to the requirements and specifications given, e.g., in USP 23rd edition Chapter 711 (Dissolution) pages 1791–1793. Referring to FIG. 14, processor 19 receives information from the ATR crystal 76 via detector 18 as the dissolution of the dosage form in the dissolution medium 4 proceeds, analyzes the information, and generates a dissolution profile of the dosage form. Most preferably, the processor receives, analyzes, and displays the dissolution profile as dissolution in the dissolution medium proceeds. Software for providing such functionality is described, for example, in PCT US00/ 23800, entitled "In Situ Methods for Measuring the Release of a Substance from a Dosage Form," the entire disclosure of which is hereby incorporated by reference. In using this apparatus, an operator preferably performs a baseline correction by taking measurements without a sample present in the vessel to obtain a baseline spectra. Thereafter, the operator places a dissolution medium and a sample material in the containment vessel. The apparatus is then used to generate spectral data from the dissolution media. The baseline spectra is then subtracted from the spectral data to provide the spectra of the dissolution medium.

What is claimed is:

1. An ATR (Attenuated Total Reflectance) crystal in situ dissolution testing system comprising:
    an ATR crystal, one face of the ATR crystal forming a portion of an interior surface of a vessel for immersing a pharmaceutical dosage form in a dissolution medium;
    a radiation source for generating a beam of radiation, the radiation source optically connected to an input of the ATR crystal;
    a detector for recording the beam of radiation, the detector optically connected to an output of the ATR crystal; and
    a processor coupled to the detector, the processor receiving information from the detector as the dissolution of the dosage form in the dissolution medium proceeds, the processor analyzing the information and generating a dissolution profile of the dosage form.

2. The ATR crystal system according to claim 1 wherein the vessel has an aperture formed therein, and the ATR crystal is secured over the aperture.

3. The embedded ATR crystal system according to claim 2 wherein the ATR crystal is secured to the vessel via an inert material.

4. The ATR system according to claim 1 wherein the radiation source is selected from the group consisting of a QTH lamp, a deuterium lamp, a light emitting diode, a laser, a Xenon Lamp, a Mercury Xenon Lamp, a Xenon Flash Lamp, a Metal Halide Lamp, a GaAs Infrared LED, a GaAlA Infrared LED, GaAlA Infrared LED, and a GaAAs Infrared LED.

5. The ATR system according to claim 1 wherein the ATR crystal is selected from the group consisting of ZnSe, Ge, SeAs, Cds, CdTe, CsI, InSb, Si, Sapphire (Al$_2$O$_3$), Annealed Glass, borosilicate crown glass, BK7 Annealed Glass, UBK7 Annealed Glass, LaSF N9 Annealed Glass, BaK1 Annealed Glass, SF11 Annealed Glass, SK11 Annealed Glass, SF5 Annealed Glass, Flint Glass, F2 Glass, Optical Crown Glass, Low-Expansion Borosilicate Glass(LEBG), Pyrex, Synthetic Fused Silica (amorphous silicon dioxide), Optical Quality Synthetic Fused Silica, UV Grade Synthetic Fused Silica, ZERODUR, AgBr, AgCl, KRS-5 (a TlBr and TlCl compound), KRS-6 (a TlBr and TlCl compound), ZnS, ZrO2, AMTIR, Fused Silica and diamond.

6. The ATR system according to claim 1 wherein the ATR crystal is coated with a material selected from the group consisting of metallic coating, dielectric coating, bare aluminum, protected aluminum, enhanced aluminum, UV-enhanced aluminum, internal silver, protected silver, bare gold, protected gold, MAXBRIte, Extended MAXBRIte, Diode Laser MAXBRIte, UV MAXBRIte, and Laser line MAX-R.

7. The ATR system according to claim 1 wherein a side of the ATR crystal opposite the interior surface of the containment vessel is coated with a material selected from the group from the group consisting of metallic coating, dielectric coating, bare aluminum, protected aluminum, enhanced aluminum, UV-enhanced aluminum, internal silver, protected silver, bare gold, protected gold, MAXBRIte, Extended MAXBRIte, Diode Laser MAXBRIte, UV MAXBRIte, and Laser line MAX-R.

8. The ATR system according to claim 1 wherein the ATR crystal is a single bounce crystal.

9. The ATR system according to claim 1 wherein the ATR crystal is a multiple bounce crystal.

10. The ATR system according to claim 1 wherein the ATR crystal is spherical in shape.

11. The ATR system according to claim 1 wherein the ATR crystal is hemispherical in shape.

12. The ATR system according to claim 1 wherein the ATR crystal is cylindrical in shape.

13. The ATR system according to claim 1 wherein the ATR crystal is trapezoidal in shape.

14. The ATR system according to claim 1 wherein the ATR crystal is rectangular in shape.

15. The ATR system according to claim 1 wherein the detectors is selected from the group consisting of Ge detectors, Si detectors, and PbS detectors.

16. The ATR system according to claim 1 wherein the detector is selected from the group consisting of PbSi photoconductive photon detectors, PbSe photon detectors, InAs photon detectors, opto-semiconductors, and InGaAs photon detectors.

17. The ATR system according to claim 1 wherein the detector is a photoconductive photon detector.

18. The ATR system according to claim 1 wherein the detector is selected from the group consisting of photovoltaic photon detectors, InSb photon detectors, photodiodes, photoconductive cells, CdS photoconductive cells, opto-semiconductors, HgCdTe photoconductive detectors, photomultiplier tubes, Ga detectors, and GaAs detectors.

19. The ATR crystal system according to claim 1 wherein the vessel includes an inert material.

20. The ATR crystal system according to claim 1 wherein the vessel is coated with polytetrafluorethylene.

21. The ATR crystal system according to claim 1 wherein the vessel includes fluoroplastic.

22. The ATR crystal system according to claim 1 wherein the ATR crystal is formed in a spiral which is attached to the interior surface of the vessel.

23. The ATR crystal system according to claim 22 wherein the spiral is comprised of fused silica.

24. The ATR crystal system according to claim 1 wherein the vessel includes polytetrafluoroethylene fluoropolymer resin.

25. The ATR crystal system according to claim 1 wherein the vessel includes steel.

26. The ATR crystal system according to claim 1 wherein the vessel includes lead.

27. The ATR system according to claim 1 wherein the radiation source is a UV light source.

28. The ATR crystal system according to claim 1 further comprising a first connecting device for transmitting light from the radiation source to the ATR crystal.

29. The ATR crystal system according to claim 28 further comprising a second connecting device for transmitting light from the ATR crystal to the detector.

30. The ATR system according to claim 29 wherein the second connecting device is a rigid wave tube.

31. The ATR system according to claim 29 wherein the second connecting device is a fiber optic cable.

32. The ATR system according to claim 29 wherein the second connecting devices is constructed from a material selected from the group consisting of Optical Glass, Fused Silica Fiber, low OH Fused Silica Fiber, Fluoride fiber, and Chalcogenide fiber.

33. The according to claim 28 wherein the first connecting device is a rigid wave tube.

34. The ATR system according to claim 28 wherein the first connecting devices is a fiber optic cable.

35. The ATR system according to claim 28 wherein the first connecting device is constructed from a material selected from the group consisting of Optical Glass, Fused Silica Fiber, low OH Fused Silica Fiber, Fluoride fiber, and Chalcogenide fiber.

36. The ATR system according to claim 1 further comprising a plurality of mirrors for directing the beam from the radiation source to the ATR crystal and from the ATR crystal to the detector.

37. The ATR system according to claim 1 wherein the radiation source is Fourier Transform devices.

38. The ATR system according to claim 1 further comprising a filter for changing polychromatic light to monochromatic light, located between the radiation source and the ATR crystal.

39. The ATR crystal system according to claim 38 wherein the filter is selected from the group consisting of a linear variable filter, spectrograph, monochromator, tilting filter wheel, interference filter, bandpass filter, interference filter mounted in an encoder wheel, pre-dispersive monochromator-based instrument, and Acousto Optic Tunable Filter using a $TeO_2$ crystal.

40. The ATR system according to claim 1 further comprising a filter for changing polychromatic light to monochromatic light, located between the ATR crystal and the detector.

41. The ATR crystal system according to claim 40 wherein the filter is selected from the group consisting of a linear variable filter, spectrograph, monochromator, tilting filter wheel, interference filter, bandpass filter, interference filter mounted in an encoder wheel, post-dispersive monochromator-based instrument, and Acousto Optic Tunable Filter using a $TeO_2$ crystal.

42. The ATR crystal system according to claim 1 further comprising a cover shaped to cover an opening in the vessel.

43. The ATR crystal system according to claim 1 further comprising a processing device.

44. The ATR crystal system according to claim 1 further comprising a mixing shaft within the vessel.

45. An apparatus for determining a dissolution profile of a pharmaceutical dosage form containing a releasable quantity of a therapeutically active agent wherein the dosage form is immersed in a dissolution medium contained in a vessel, comprising:

a vessel for immersing a pharmaceutical dosage form in a dissolution medium;

an elongated probe including an ATR (Attenuated Total Reflectance) crystal, the elongated probe disposed within the vessel such that the ATR crystal is immersed in the dissolution medium;

a radiation source for creating a beam of radiation, the radiation source optically connected to an input of the ATR crystal;

a detector for recording the beam of radiation, the detector optically connected to an output of the ATR crystal; and a processor coupled to the detector, the processor receiving information from the detector as the dissolution of the dosage form in the dissolution medium proceeds, the processor analyzing the information and generating a dissolution profile of the dosage form.

46. The ATR crystal system according to claim 45 wherein the ATR crystal is shaped as an elongated cylinder.

47. The ATR crystal system according to claim 46 further comprising a cover for covering a portion of the elongated cylindrical ATR crystal.

48. The ATR crystal system according to claim 47 wherein the cover is composed of an inert material.

49. The ATR system according to claim 45 wherein the radiation source is selected from the group consisting of a QTH lamp, a deuterium lamp, a light emitting diode, a laser, a Xenon Lamp, a Mercury Xenon Lamp, a Xenon Flash Lamp, a Metal Halide Lamp, a GaAs Infrared LED, a GaAlA Infrared LED, GaAlA Infrared LED, and a GaAAs Infrared LED.

50. The ATR system according to claim 45 wherein the ATR crystal is selected from the group consisting of ZnSe, Ge, SeAs, Cds, CdTe, CsI, InSb, Si, Sapphire ($Al_2O_3$), Annealed Glass, borosilicate crown glass, BK7 Annealed Glass, UBK7 Annealed Glass, LaSF N9 Annealed Glass, BaK1 Annealed Glass, SF11 Annealed Glass, SK11 Annealed Glass, SF5 Annealed Glass, Flint Glass, F2 Glass, Optical Crown Glass, Low-Expansion Borosilicate Glass (LEBG), Pyrex, Synthetic Fused Silica (amorphous silicon dioxide), Optical Quality Synthetic Fused Silica, UV Grade Synthetic Fused Silica, ZERODUR, AgBr, AgCl, KRS-5 (a TlBr and TlCl compound), KRS-6 (a TlBr and TlCl compound), ZnS, ZrO2, AMTIR, Fused Silica, and diamond.

51. The ATR system according to claim 45 wherein the ATR crystal is coated with a material selected from the group from the group consisting of metallic coating, dielectric coating, bare aluminum, protected aluminum, enhanced aluminum, UV-enhanced aluminum, internal silver, protected silver, bare gold, protected gold, MAXBRIte, Extended MAXBRIte, Diode Laser MAXBRIte, UV MAXBRIte, and Laser line MAX-R.

52. The ATR system according to claim 45 wherein the ATR crystal is a single bounce crystal.

53. The ATR system according to claim 45 wherein the ATR crystal is a multiple bounce crystal.

54. The ATR system according to claim 45 wherein the ATR crystal is spherical in shape.

55. The ATR system according to claim 45 wherein the ATR crystal is hemispherical in shape.

56. The ATR system according to claim 45 wherein the ATR crystal is cylindrical in shape.

57. The ATR system according to claim 45 wherein the ATR crystal is trapezoidal in shape.

58. The ATR system according to claim 45 wherein the ATR crystal is rectangular in shape.

59. The ATR system according to claim 45 wherein the detector is selected from the group consisting of Ge detectors, Si detectors, and PbS detectors.

60. The ATR system according to claim 45 wherein the detector is selected from the group consisting of PbSi photoconductive photon detectors, PbSe photon detectors, InAs photon detectors, opto-semiconductors, and InGaAs photon detectors.

61. The ATR system according to claim 45 wherein the detector is a photoconductive photon detector.

62. The ATR system according to claim 45 wherein the detector is selected from the group consisting of photovoltaic photon detectors, InSb photon detectors, photodiodes, photoconductive cells, CdS photoconductive cells, opto-semiconductors, HgCdTe photoconductive detectors, photomultiplier tubes, Ga detectors, and GaAs detectors.

63. The ATR crystal system according to claim 45 wherein the probe includes a first chalcogenide fiber for directing radiation into the input of the ATR crystal, and a second chalcogenide fiber for receiving the beam radiation from the output of the ATR crystal.

64. The ATR crystal system according to claim 45 wherein the probe is clad with a glass with a refractive index lower than the probe.

65. The ATR crystal system according to claim 45 wherein the vessel includes an inert material.

66. The ATR crystal system according to claim 45 wherein the vessel is coated with polytetrafluorethylene.

67. The ATR crystal system according to claim 45 wherein the vessel-includes fluoroplastic.

68. The ATR crystal system according to claim 45 wherein the vessel-includes polytetrafluorethylene fluoropolymer resin.

69. The ATR crystal system according to claim 45 wherein the vessel includes steel.

70. The ATR crystal system according to claim 45 wherein the vessel-includes lead.

71. The ATR crystal system according to claim 45 wherein the probe-comprises an inert material.

72. The ATR crystal system according to claim 45 wherein the probe is coated with polytetrafluorethylene.

73. The ATR crystal system according to claim 45 wherein the probe comprises fluoroplastic.

74. The ATR crystal system according to claim 45 wherein the probe is polytetrafluorethylene fluoropolymer resin.

75. The ATR system according to claim 45 wherein the radiation source is a UV light source.

76. The ATR crystal system according to claim 45 further comprising a first connecting device for transmitting light from a radiation source to the ATR crystal.

77. The ATR crystal system according to claim 76 further comprising a second connecting device for transmitting light from the ATR crystal to the detector.

78. The ATR system according to claim 77 wherein the second connecting device is embedded in the probe.

79. The ATR system according to claim 77 wherein the second connecting device is a rigid wave tube.

80. The ATR system according to claim 77 wherein the second connecting device is a fiber optic cable.

81. The ATR system according to claim 77 wherein the second connecting device is constructed from a material selected from the group consisting of Optical Glass, Fused Silica Fiber, low OH Fused Silica Fiber, Fluoride fiber, and Chalcogenide fiber.

82. The ATR system according to claim 76 wherein the first connecting device is embedded in the probe.

83. The ATR system according to claim 76 wherein the first connecting devices is a rigid wave tube.

84. The ATR system according to claim 76 wherein the first connecting devices is a fiber optic cable.

85. The ATR system according to claim 76 wherein the first connecting devices is constructed from a material selected from the group consisting of Optical Glass, Fused Silica Fiber, low OH Fused Silica Fiber, Fluoride fiber, and Chalcogenide fiber.

86. The ATR system according to claim 45 further comprising a plurality of mirrors for directing the beam from the radiation source to the probe and from the probe to the detector.

87. The ATR system according to claim 45 wherein the radiation source is an Fourier Transform devices.

88. The ATR crystal system according to claim 45 further comprising a first internal connecting device and a second internal connecting device, arranged so that the first internal connecting device contacts the input of the ATR crystal and an input of the probe, and the second internal connecting device contacts the output of the ATR crystal and an output of the probe.

89. The ATR system according to claim 45 further comprising a filter for changing polychromatic light to monochromatic light, located between the radiation source and the ATR crystal.

90. The ATR crystal system according to claim 89 wherein the filter is selected from the group consisting of a linear variable filter, spectrograph, monochromator, tilting filter wheel, interference filter, bandpass filter, interference filter mounted in an encoder wheel, pre-dispersive monochromator-based instrument, and Acousto Optic Tunable Filter using a $TeO_2$ crystal.

91. The ATR system according to claim 45 further comprising a filter for changing polychromatic light to monochromatic light, located between the ATR crystal and the detector.

92. The ATR crystal system according to claim 91 wherein the filter is selected from the group consisting of a linear variable filter, spectrograph, monochromator, tilting filter wheel, interference filter, bandpass filter, interference filter mounted in an encoder wheel, post-dispersive monochromator-based instrument, and Acousto Optic Tunable Filter using a $TeO_2$ crystal.

93. The ATR crystal system according to claim 45 further comprising a securing device for preventing motion of the probe.

94. The ATR crystal system according to claim 93 wherein the securing device is a screw.

95. The ATR crystal system according to claim 45 further comprising a processing device.

96. An apparatus for determining a dissolution profile of a pharmaceutical dosage form containing a releasable quantity of a therapeutically active agent wherein the dosage form is immersed in a dissolution medium contained in a vessel, comprising:

a vessel for immersing a pharmaceutical dosage form in a dissolution medium, the vessel having an ATR crystal, one face of the ATR (Attenuated Total Reflectance) crystal forming a portion of an interior surface of the vessel;

a radiation source for creating a beam of radiation, the radiation source optically connected to an input of the ATR crystal;

a detector for recording the beam of radiation, the detector optically connected to an output of the ATR crystal;

a processor coupled to the detector, the processor receiving information from the ATR crystal as the dissolution of the dosage form in the dissolution medium proceeds, the processor analyzing the information and generating a dissolution profile of the dosage form.

97. The apparatus of claim 96, wherein the processor continuously receives information from the ATR crystal as the dissolution of the dosage form in the dissolution medium proceeds, the processor analyzing the information and continuously generating a dissolution profile of the dosage form as the dissolution of the dosage form in the dissolution medium proceeds.

98. The apparatus of claim 96, further comprising a rotatable mixing shaft disposed within the vessel.

99. The apparatus of claim 96, wherein the vessel contains an agitation device.

100. The apparatus of claim 99, wherein the agitation device comprises a paddle attached to a shaft.

101. The apparatus of claim 99, wherein the agitation device comprises a rotating basket attached to a shaft.

102. The apparatus of claim 96, wherein determining a dissolution profile of a pharmaceutical dosage form comprises a U.S.P. dissolution monograph.

103. The apparatus of claim 96, wherein determining a dissolution profile of a pharmaceutical dosage form comprises a U.S.P. drug release test.

104. The apparatus of claim 96, wherein the ATR crystal is shaped to fit in an aperture of the containment vessel.

105. A method for determining a dissolution profile of a pharmaceutical dosage form containing a releasable quantity of a therapeutically active agent comprising the steps of:

(a) immersing a pharmaceutical dosage form in a dissolution medium, the dosage form and the dissolution medium being contained within a vessel, the vessel having an ATR (Attenuated Total Reflectance) crystal, one face of the ATR crystal forming a portion of an interior surface of the vessel;

(b) receiving information from a detector which is optically connected to the ATR crystal as dissolution of the dosage form in the dissolution medium proceeds; and (c) processing the information received from the detector in step (b) and generating a dissolution profile of the dosage form.

106. The method of claim 105, further comprising the step of displaying the dissolution profile of the active agent on a display device as a percentage of active agent released versus time.

107. The method of claim 105, wherein the receiving step includes continuously receiving information from the ATR crystal as the dissolution of the dosage form in the dissolution medium proceeds, and wherein the analyzing and generating step includes analyzing the information and continuously generating a dissolution profile of the dosage form as the dissolution of the dosage form in the dissolution medium proceeds.

108. A method for determining a dissolution profile of a pharmaceutical dosage form containing a releasable quantity of a therapeutically active agent, comprising the steps of:

(a) immersing a pharmaceutical dosage form in a dissolution medium, the dosage form and the dissolution medium being contained within a vessel, an elongated probe including an ATR (Attenuated Total Reflectance) crystal disposed within the vessel such that the ATR crystal is immersed in the dissolution medium;

(b) receiving information from a detector which is optically connected to the ATR crystal as dissolution of the dosage form in the dissolution medium proceeds; and (c) processing the information received from the detector in step (b) and generating a dissolution profile of the dosage form.

\* \* \* \* \*